US010327860B2

(12) United States Patent
Matsuda et al.

(10) Patent No.: US 10,327,860 B2
(45) Date of Patent: Jun. 25, 2019

(54) MEASUREMENT INSTRUMENT FOR JOINT SURGERY

(71) Applicant: KYOCERA Medical Corporation, Osaka-shi, Osaka (JP)

(72) Inventors: Shuichi Matsuda, Kyoto (JP); Masahiko Hashida, Osaka (JP); Yuichi Enomoto, Osaka (JP)

(73) Assignee: KYOCERA CORPORATION, Kyoto (JP)

( * ) Notice: Subject to any disclaimer, the term of this patent is extended or adjusted under 35 U.S.C. 154(b) by 138 days.

(21) Appl. No.: 15/307,882

(22) PCT Filed: Jun. 17, 2015

(86) PCT No.: PCT/JP2015/067459
§ 371 (c)(1),
(2) Date: Oct. 31, 2016

(87) PCT Pub. No.: WO2015/194589
PCT Pub. Date: Dec. 23, 2015

(65) Prior Publication Data
US 2017/0049527 A1     Feb. 23, 2017

(30) Foreign Application Priority Data

Jun. 19, 2014   (JP) .................. 2014-126135

(51) Int. Cl.
*A61B 17/56*     (2006.01)
*A61B 90/00*     (2016.01)
(Continued)

(52) U.S. Cl.
CPC ............ *A61B 90/06* (2016.02); *A61B 5/1075* (2013.01); *A61B 5/1121* (2013.01); *A61B 5/4528* (2013.01); *A61B 17/88* (2013.01)

(58) Field of Classification Search
CPC ..... A61B 90/06; A61B 5/1075; A61B 5/1121; A61B 5/4528; A61B 5/4504; A61B 5/4585; A61B 17/56; A61B 17/88
(Continued)

(56) References Cited

U.S. PATENT DOCUMENTS 4,570,349 A * 2/1986 Finkelman ............... G01B 7/02
                                                          33/501
4,718,850 A * 1/1988 Knebelman ............ A61C 19/04
                                                          33/513
(Continued)

FOREIGN PATENT DOCUMENTS

JP    09-502621 A    3/1997
JP    2007-075517 A  3/2007
(Continued)

OTHER PUBLICATIONS

International Search Report, PCT/JP2015/067459, dated Sep. 29, 2015, 2 pgs.
(Continued)

*Primary Examiner* — Zade Coley
*Assistant Examiner* — Jessica Weiss
(74) *Attorney, Agent, or Firm* — Volpe and Koenig, P.C.

(57) ABSTRACT

A measurement instrument for joint surgery may relatively move a first bone and a second bone, which are connected by soft tissue at a joint, in directions other than directions in which these bones are separated from each other, and measure the stability of a connection state between these bones. A housing may be fixed to a first bone. A slider may slide relative to the housing, and abut against a second bone. A position display portion displays the position of the slider relative to the housing. A measurement instrument for joint surgery relatively moves the second bone relative to the first bone along a joint face by the slider sliding relative to the
(Continued)

housing. The stability of a state of connection between the first bone and the second bone is measured based on the position of the slider relative to the housing displayed by the position display portion.

6 Claims, 19 Drawing Sheets

(51) Int. Cl.
  *A61B 5/11* (2006.01)
  *A61B 5/00* (2006.01)
  *A61B 17/88* (2006.01)
  *A61B 5/107* (2006.01)

(58) Field of Classification Search
  USPC ....... 606/102, 87–90; 33/512–513, 712, 783, 33/806, 809–811, 813, 815
  See application file for complete search history.

(56) References Cited

U.S. PATENT DOCUMENTS

| | | | | |
|---|---|---|---|---|
| 4,731,931 A | * | 3/1988 | Goodman | G01B 3/20 33/520 |
| 4,843,720 A | * | 7/1989 | Kim | A61B 5/107 33/512 |
| 4,938,230 A | * | 7/1990 | Machek | A61B 1/24 33/514 |
| 5,082,003 A | * | 1/1992 | Lamb | A61B 5/1076 33/512 |
| 5,176,516 A | * | 1/1993 | Koizumi | A61C 19/04 33/513 |
| 5,213,112 A | * | 5/1993 | Niwa | A61B 17/025 600/587 |
| 5,318,571 A | | 6/1994 | Benson | |
| 6,105,269 A | * | 8/2000 | Kondrat | A61B 5/4504 33/512 |
| 6,361,506 B1 | * | 3/2002 | Saenger | A61B 5/1071 33/512 |
| 6,430,830 B1 | * | 8/2002 | Segal | A61C 19/04 33/513 |
| 7,615,055 B2 | * | 11/2009 | DiSilvestro | A61F 2/461 606/88 |
| 7,841,098 B2 | * | 11/2010 | Richter | G01B 5/061 33/512 |
| 8,197,489 B2 | * | 6/2012 | Chessar | A61B 17/025 606/90 |
| 8,438,748 B1 | * | 5/2013 | Moon | G01B 5/0002 33/783 |
| 8,931,185 B2 | * | 1/2015 | Emtman | G01B 3/205 33/784 |
| 2004/0122441 A1 | * | 6/2004 | Muratsu | A61B 17/0206 606/102 |
| 2006/0155295 A1 | * | 7/2006 | Supper | A61B 17/025 606/90 |
| 2008/0275509 A1 | | 11/2008 | Clifford et al. | |
| 2009/0326544 A1 | * | 12/2009 | Chessar | A61B 17/025 606/102 |
| 2013/0013067 A1 | | 1/2013 | Landry et al. | |
| 2014/0358231 A1 | | 12/2014 | Landry et al. | |

FOREIGN PATENT DOCUMENTS

| | | |
|---|---|---|
| JP | 2011-519303 A | 7/2011 |
| JP | 2014-525772 A | 10/2014 |
| WO | 2013/006291 A2 | 1/2013 |

OTHER PUBLICATIONS

Family List for Japanese Patent Application No. 2011-519303 (Jul. 7, 2011), 17 pgs.
Family List for Japanese Patent Application No. 09-502621 (Mar. 18, 1997), 2 pgs.

\* cited by examiner

US 10,327,860 B2

MEASUREMENT INSTRUMENT FOR JOINT SURGERY

TECHNICAL FIELD

The present invention relates to a measurement instrument for joint surgery that is used in joint surgery in order to measure the stability of a state of connection between a first bone and a second bone that are connected by soft tissue at a joint.

BACKGROUND ART

Bones connected at a joint are connected by soft tissue, which includes ligaments. In joint surgery, the stability (lability) of a state of connection between a first bone and a second bone that are connected by soft tissue at a joint is checked. More specifically, in joint surgery, a surgeon checks the stability of the state of connection between the first bone and the second bone by relatively moving the first bone and the second bone and ascertaining the state of movement. For example, in the case of joint surgery for a knee joint, the surgeon checks the stability of the state of connection between the tibia and the femur by relatively moving the femur with respect to the tibia or relatively moving the tibia with respect to the femur, and ascertaining the state of the movement.

An instrument disclosed in Patent Document 1 is known as an instrument that can be used in knee joint surgery to check the stability of the state of connection between the tibia and the femur. The instrument disclosed in Patent Document 1 is constituted by a femur-attached member that is attached to the femur, and a jig body that abuts against a proximal end face of the tibia and a distal end face of the femur that are formed by excision. The femur-attached member and the jig body are connected so as to be able to relatively move in a direction perpendicular to the proximal end face of the tibia and be locked at any relative position, in order to cause a state of tension in the soft tissue that connects the tibia and the femur.

More specifically, in the instrument disclosed in Patent Document 1, the femur-attached member has a rod portion that is inserted into the femur along an axis thereof from the distal end face of the femur, and a cylindrical portion that extends in a direction perpendicular to the axis. The jig body has a spacer arranged on the proximal end face of the tibia, and a movable block that is fixed to the spacer in a removable manner and abuts against the distal end face of the femur. Furthermore, the movable block has a drive screw capable of rotating while meshing with the cylindrical portion of the femur-attached member. The drive screw is rotationally driven by a hexagonal wrench. Due to the drive screw being rotationally driven, the femur-attached member and the movable block are driven so as to relatively move with respect to each other. Thus, the instrument disclosed in Patent Document 1 is configured to be able to relatively move the tibia and the femur in separating directions and cause a state of tension in the soft tissue. The surgeon uses this instrument to relatively move the tibia and the femur in separating directions and check the stability of the state of connection between the tibia and the femur.

CITATION LIST

Patent Document

Patent Document 1: JP 2007-75517A

DISCLOSURE OF THE INVENTION

Problem To be Solved by the Invention

The instrument disclosed in Patent Document 1 relatively moves, in separating directions, the first bone and the second bone that are connected by soft tissue at a joint, and causes a state of tension in the soft tissue, as mentioned above. Then, the surgeon checks the stability of the state of connection between the first bone and the second bone in a state where the first bone and the second bone have been relatively moved in separating direction using this instrument.

As described above, the instrument disclosed in Patent Document 1 can only relatively move the first bone and the second bone in separating directions. On the other hand, in joint surgery, in order to enable a more accurate check of the stability of the state of connection between bones at a joint, it is also favorable to cause a state of tension in soft tissue by relatively moving a first bone and a second bone in directions other than directions in which these bones are separated from each other, and check the stability of the state of connection between the bones at the joint. Accordingly, achievement of an instrument that causes a state of tension in soft tissue by relatively moving the first bone and the second bone in directions other than directions in which these bones are separated from each other is desired. Furthermore, in order to be able to more accurately check the stability of the state of connection between bones at a joint, it is favorable that, when the first bone and the second bone are relatively moved in directions other than directions in which these bones are separated from each other, the state of the movement can be quantified, and the stability of the state of connection between these bones can be measured.

In view of the foregoing situation, an object of the present invention is to provide a measurement instrument for joint surgery that can relatively move a first bone and a second bone that are connected by soft tissue at a joint, in directions other than directions in which these bones are separated from each other, and measure the stability of a state of connection between these bones.

Means for Solving the Problem (1) The present invention relates to a measurement instrument for joint surgery that is used in joint surgery in order to measure stability of a state of connection between a first bone and a second bone that are connected by soft tissue at a joint. A measurement instrument for joint surgery according to the present invention for achieving the above-stated object includes: a slider that is provided so as to be able to slide with respect to the housing, and can abut against or be fixed to the second bone or a component attached to the second bone; and a position display portion that displays a position of the slider relative to the housing, wherein the second bone is relatively moved with respect to the first bone along a joint face that is between the first bone and the second bone by the slider sliding relative to the housing, and the stability of the state of connection between the first bone and the second bone is measured based on the position of the slider relative to the housing, the position being displayed by the position display portion.

With this configuration, the housing is fixed to the first bone or the component attached to the first bone. Meanwhile, the slider is arranged in a state of being fixed to or abutting against the second bone or the component attached to the second bone. In this state, the measurement instrument for joint surgery is operated such that the slider slides relative to the housing. Thus, the second bone is relatively moved with respect to the first bone along the joint face. The amount of relative movement when the second bone relatively moves with respect to the first bone along the joint face is measured based on the position of the slider relative to the housing that is displayed by the position display portion. Thus, with this measurement instrument for joint surgery, the first bone and the second bone that are connected by soft tissue at a joint are relatively moved along the joint face therebetween, and the stability of a state of connection between these bones is measured as the amount of relative movement in the direction along this joint face. That is to say, with this measurement instrument for joint surgery, the first bone and the second bone can be relatively moved in directions other than directions in which these bones are separated from each other, and the stability of the state of connection between these bones can be measured.

As described above, according to the present invention, it is possible to provide a measurement instrument for joint surgery that can relatively move the first bone and the second bone that are connected by soft tissue at a joint, in directions other than directions in which these bones are separated from each other, and measure the stability of the state of connection between these bones.

(2) In the above measurement instrument for joint surgery, it is preferable that the housing is provided with a first bone contact portion provided so as to project in a cantilevered manner from a body part of the housing, the first bone contact portion coming into contact with and being fixed to the first bone or the component attached to the first bone, the slider is provided with a second bone contact portion provided so as to project in a cantilevered manner from a body part of the slider, the second bone contact portion coming into contact with and abutting against or being fixed to the second bone or the component attached to the second bone, and the first bone contact portion and the second bone contact portion extend in a cantilevered manner in opposite directions that are parallel with a direction intersecting a sliding direction of the slider relative to the housing.

With this configuration, the first bone contact portion and the second bone contact portion extend in a cantilevered manner in opposite directions that are parallel with a direction intersecting the sliding direction of the slider relative to the housing. Therefore, a mechanism that relatively moves the second bone with respect to the first bone along the joint face by the slider sliding relative to the housing can be achieved with a simple structure that includes the first and second bone contact portions which project in a cantilevered manner respectively from the housing and the slider.

(3) It is preferable that the housing includes: a housing body that slidably supports the slider; and a component fixing portion that is detachably attached to the housing body and is provided so as to be able to be fixed to the component attached to the first bone.

With this configuration, the stability of the state of connection between the first bone and the second bone can be measured using the measurement instrument for joint surgery in both states where the component is attached to the first bone and not attached to the first bone. That is to say, in the state where the component is attached to the first bone, the measurement instrument for joint surgery can be used by attaching the component fixing portion to the housing body. On the other hand, in the state where the component is not attached to the first bone, the measurement instrument for joint surgery can be used after removing the component fixing portion from the housing body.

(4) In the above measurement instrument for joint surgery, it is preferable that the position display portion is provided with a gauge that is provided in one of the housing and the slider, and a reading position indicating portion that is provided in the other one of the housing and the slider and indicates a reading position in the gauge.

With this configuration, the position display portion that displays the position of the slider relative to the housing can be achieved with a simple structure in which one of the housing and the slider is provided with the gauge, and the other one is provided with the reading position indicating portion.

(5) In the above measurement instrument for joint surgery, it is preferable to further include a drive mechanism that drives the slider so as to slide relative to the housing.

With this configuration, the slider is slid relative to the housing via the drive mechanism. Therefore, the slider can be relatively moved with respect to the housing in a smooth and accurate manner. Therefore, the second bone can be relatively moved with respect to the first bone along the joint face in a smooth and accurate manner.

(6) In the above measurement instrument for joint surgery, it is preferable that the drive mechanism includes: a driving force input portion to which a driving force in a rotational direction from outside is input; and a sliding drive portion that converts the driving force in the rotational direction, the driving force being input to the driving force input portion, into a driving force in a linear direction, and slides the slider relative to the housing.

With this configuration, upon a driving force in the rotational direction from the outside being input, this driving force in the rotational direction is converted into a driving force in the linear direction, and the slider slides relative to the housing. Therefore, the slider can be relatively moved with respect to the housing in a smooth and accurate manner using the torque driver that generates the driving force in the rotational direction. Furthermore, since the torque driver can be used, the torque that is input by the torque driver can be measured by the torque driver. Thus, in relation to the measurement of the stability of the state of connection between the first bone and the second bone in directions other than direction in which these bones are separated from each other, a tensile force generated by soft tissue that connects these bones can also be readily measured.

(7) In the above measurement instrument for joint surgery, it is preferable that the housing is provided with a first chamfered portion or a first curved portion having a curved surface that curves, on a corner at an end of the body part of the housing, the end at which the first bone contact portion projects, the corner being on a side opposite to a side where the first bone contact portion projects, and the slider is provided with a second chamfered portion or a second curved portion having a curved surface that curves, on a corner at an end of the body part of the slider, the end at which the second bone contact portion projects, the corner being on a side opposite to a side where the second bone contact portion projects.

With this configuration, since the first chamfered portion or the first curved portion is provided in the housing, it is possible to prevent the second bone and the corner of the housing on the side opposite to the side where the first bone contact portion projects from coming into contact and interfering with each other. In addition, since the second chamfered portion or the second curved portion is provided in the slider, it is possible to prevent the first bone and the corner of the slider on the side opposite to the side where the second bone contact portion projects from coming into contact and interfering with each other. Accordingly, when the second bone is relatively moved with respect to the first bone along the joint face by the measurement instrument for joint surgery, or when the angle of a joint constituted by an end of the first bone and an end of the second bone is changed with the measurement instrument for joint surgery arranged near the joint, it is possible to prevent the occurrence of interference between the first and second bones and the measurement instrument for joint surgery due to contact that is not intended by the surgeon.

EFFECTS OF THE INVENTION

The present invention can provide a measurement instrument for joint surgery that can relatively move a first bone and a second bone that are connected by soft tissue at a joint, in directions other than directions in which these bones are separated from each other, and measure the stability of a state of connection between these bones.

DESCRIPTION OF EMBODIMENTS

Hereinafter, modes for carrying out the present invention will be described with reference to the drawings. Note that the present invention can be widely applied as a measurement instrument for joint surgery that is used in joint surgery in order to measure the stability of a state of connection between a first bone and a second bone that are connected by soft tissue at a joint.

First Embodiment

Overview of Measurement Instrument for Joint Surgery

Figure 1:
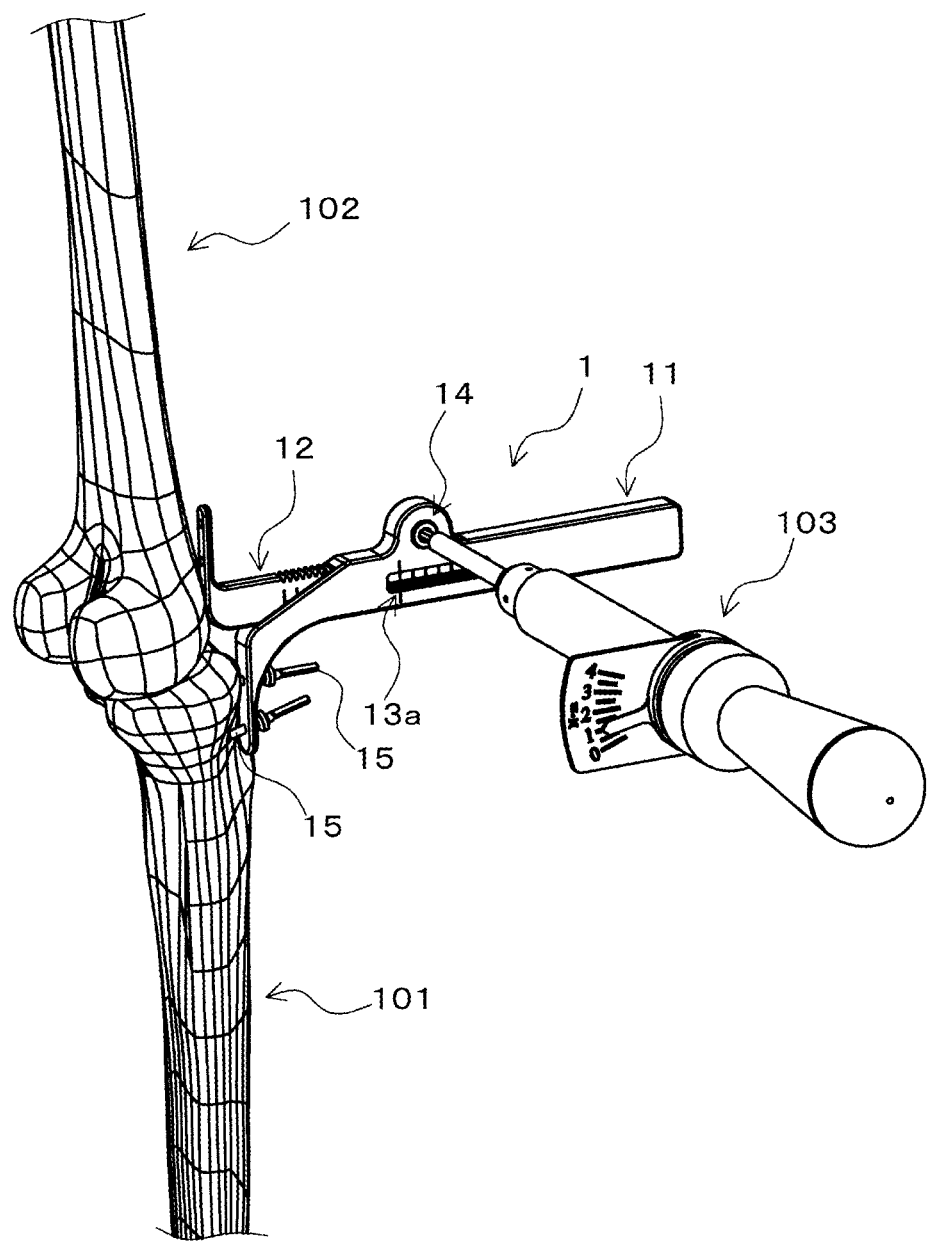
FIG. 1 is a schematic view showing a form of use of a measurement instrument for joint surgery according to a first embodiment of the present invention.
Figure 2:
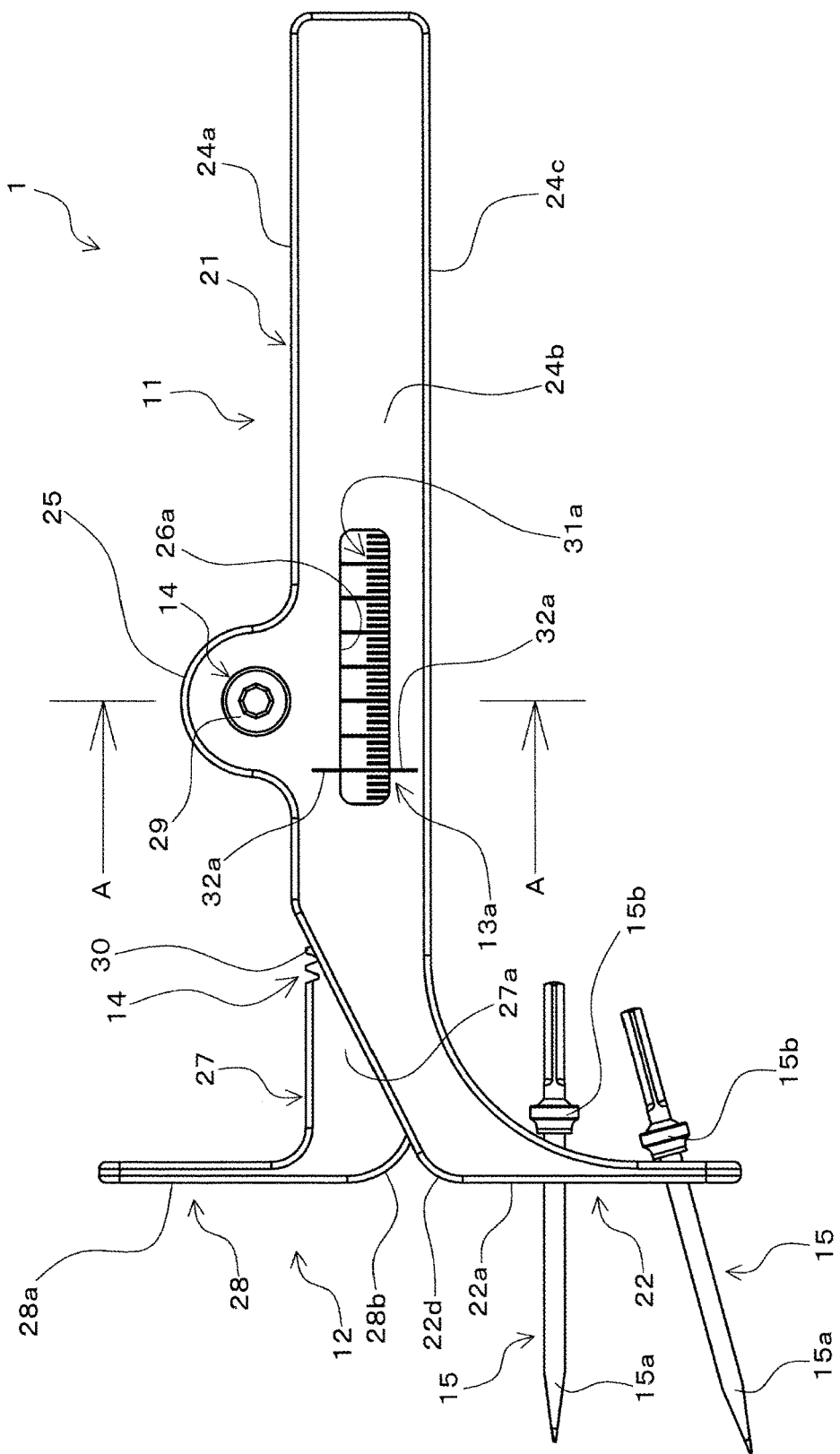
FIG. 2 is a front view of the measurement instrument for joint surgery shown in FIG. 1.
Figure 3:
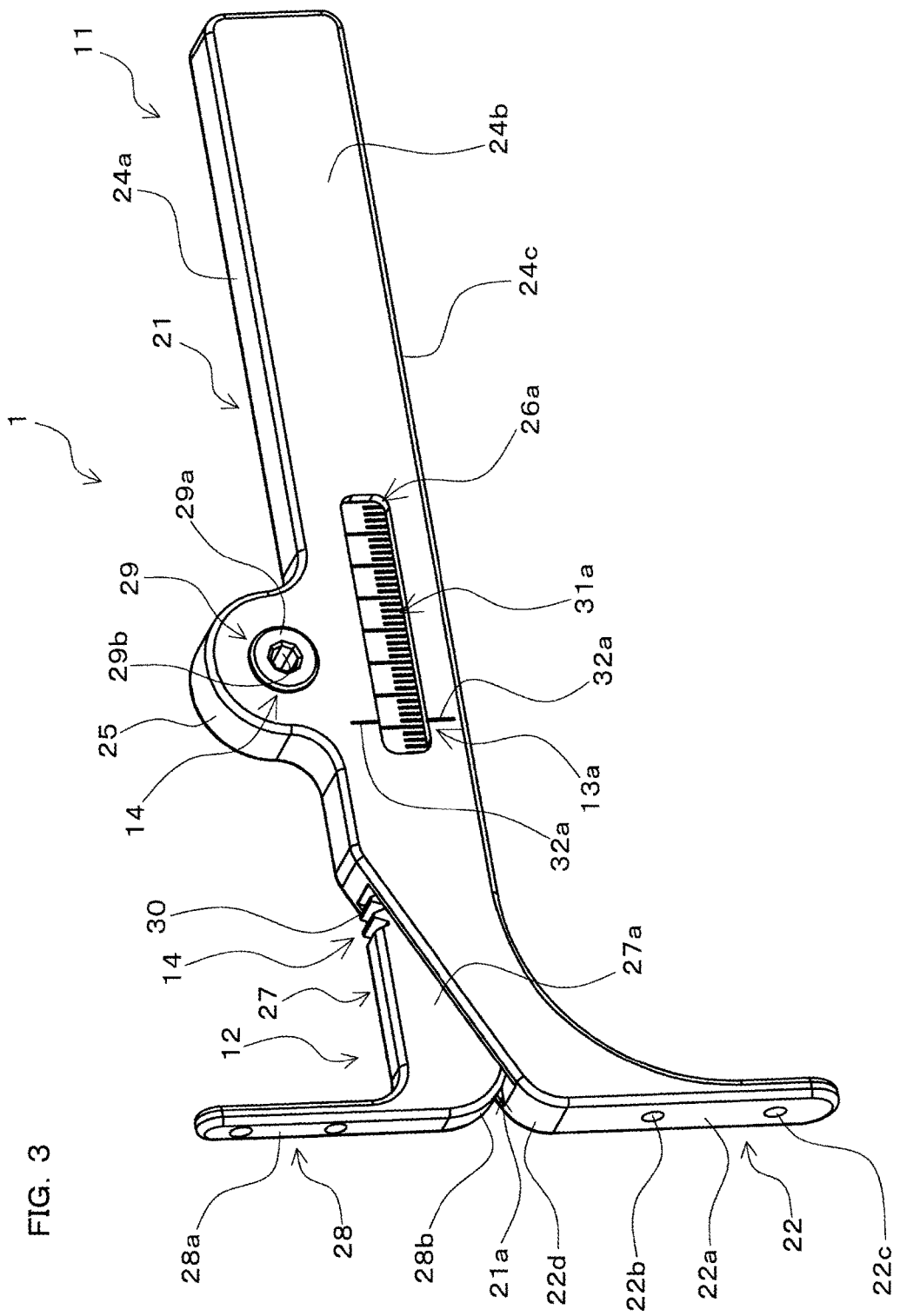
FIG. 3 is a perspective view of the measurement instrument for joint surgery shown in FIG. 1.
Figure 4:
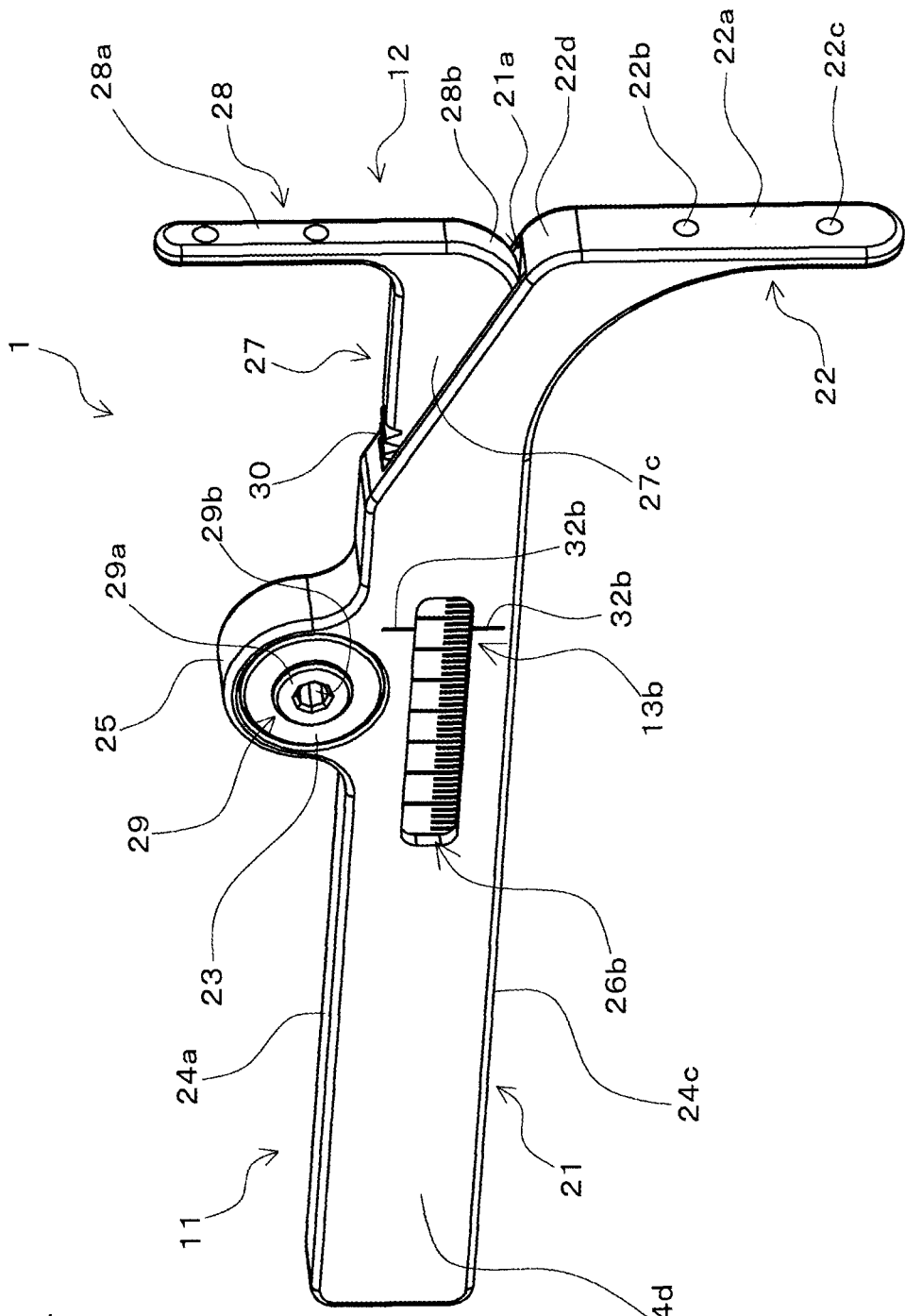
FIG. 4 is a perspective view of the measurement instrument for joint surgery shown in FIG. 1, as viewed from a direction different from the direction in FIG. 3.
Figure 5:
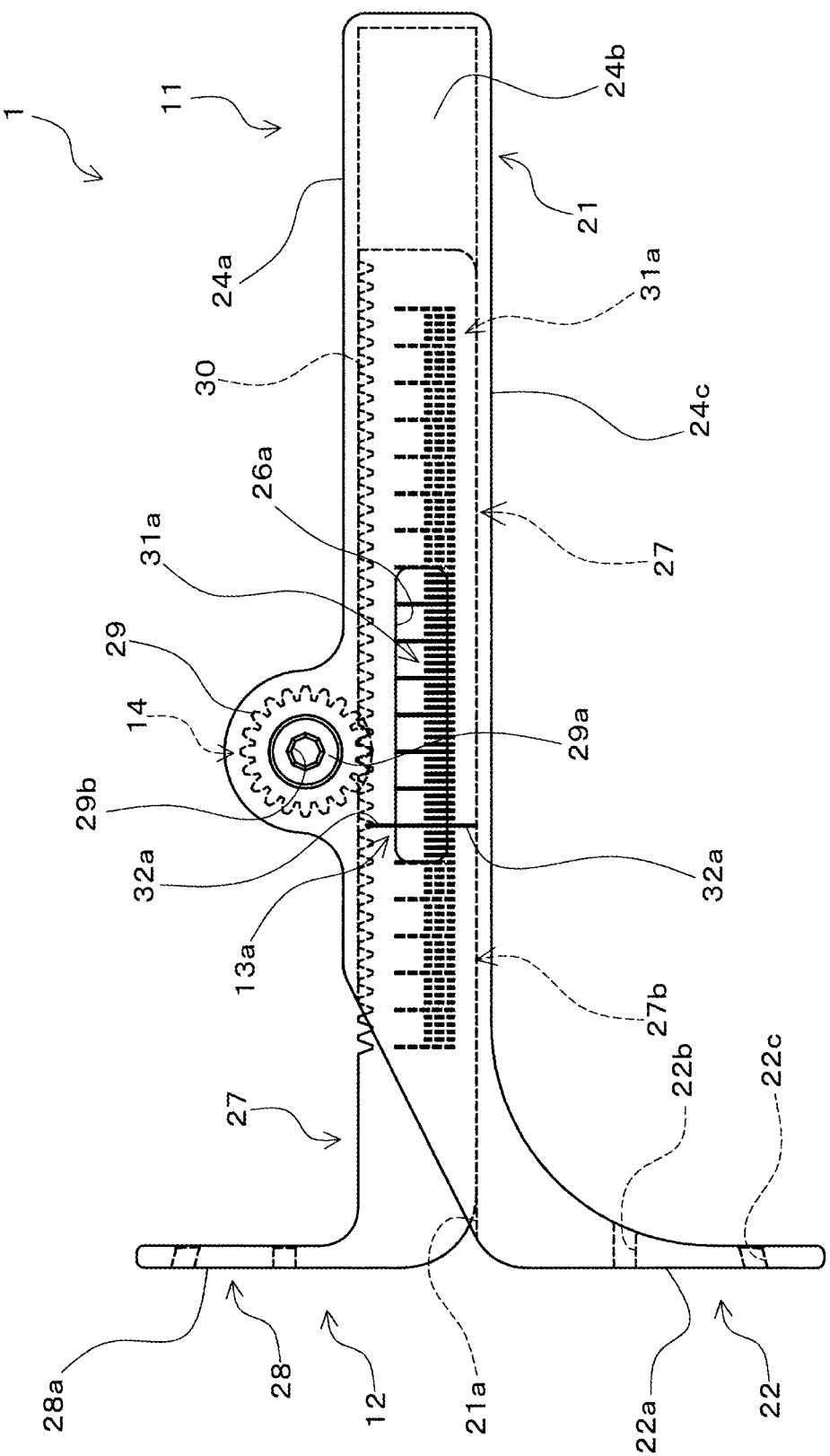
FIG. 5 is a front view of the measurement instrument for joint surgery shown in FIG. 1, with an internal structure indicated by broken lines.

FIG. 1 is a schematic view showing a form of use of a measurement instrument for joint surgery 1 according to a first embodiment of the present invention. FIG. 2 is a front view of the measurement instrument for joint surgery 1. FIG. 3 is a perspective view of the measurement instrument for joint surgery 1. FIG. 4 is a perspective view of the measurement instrument for joint surgery 1 as viewed from a direction different from that in FIG. 3. FIG. 5 is a front view of the measurement instrument for joint surgery 1, with an internal structure indicated by broken lines.

The measurement instrument for joint surgery 1 shown in FIGS. 1 to 5 is used in joint surgery. The measurement instrument for joint surgery 1 can be used in various types of joint surgery. For example, the measurement instrument for joint surgery 1 can be used in artificial joint replacement surgery for replacing a joint with an artificial joint, in order to check the stability of the joint before the artificial joint is installed. Furthermore, the measurement instrument for joint surgery 1 can also be used to check the stability of the joint after the artificial joint is installed, and the measurement instrument for joint surgery 1 can also be used in joint surgery in which replacement with an artificial joint is not performed.

The measurement instrument for joint surgery 1 can also be used in the case where a joint is in an angle state of either an extension position or a bending position in knee joint surgery, elbow joint surgery, and foot joint surgery, for example. Note that this embodiment will describe the measurement instrument for joint surgery 1 taking, as an example, a mode used in the case where a knee joint is at an extension position among the modes used in knee joint surgery. However, the measurement instrument for joint surgery 1 can also be used similarly in the case where a knee joint is at a bending position.

The measurement instrument for joint surgery 1 is provided as an instrument that is used in knee joint surgery in order to measure the stability (lability) of a state of connection between a tibia 101 and a femur 102 that are connected by soft tissue such as ligaments, at a knee joint. The tibia 101 serves as a first bone in this embodiment, and the femur 102 serves as a second bone in this embodiment. Note that the schematic view in FIG. 1 omits human tissue other than the tibia 101 and the femur 102. The schematic view in FIG. 1 shows the tibia 101 and the femur 102 only in the region of the knee joint and the periphery thereof.

The measurement instrument for joint surgery 1 is constituted by a housing 11, a slider 12, position display portions (13a and 13b), a drive mechanism 14, and the like. Note that FIG. 2 also shows fixation pins 15 that are used together with the measurement instrument for joint surgery 1. Note that the housing 11, the slider 12, and the drive mechanism 14 are made of a metallic material such as stainless steel, for example.

Housing

Figure 6:
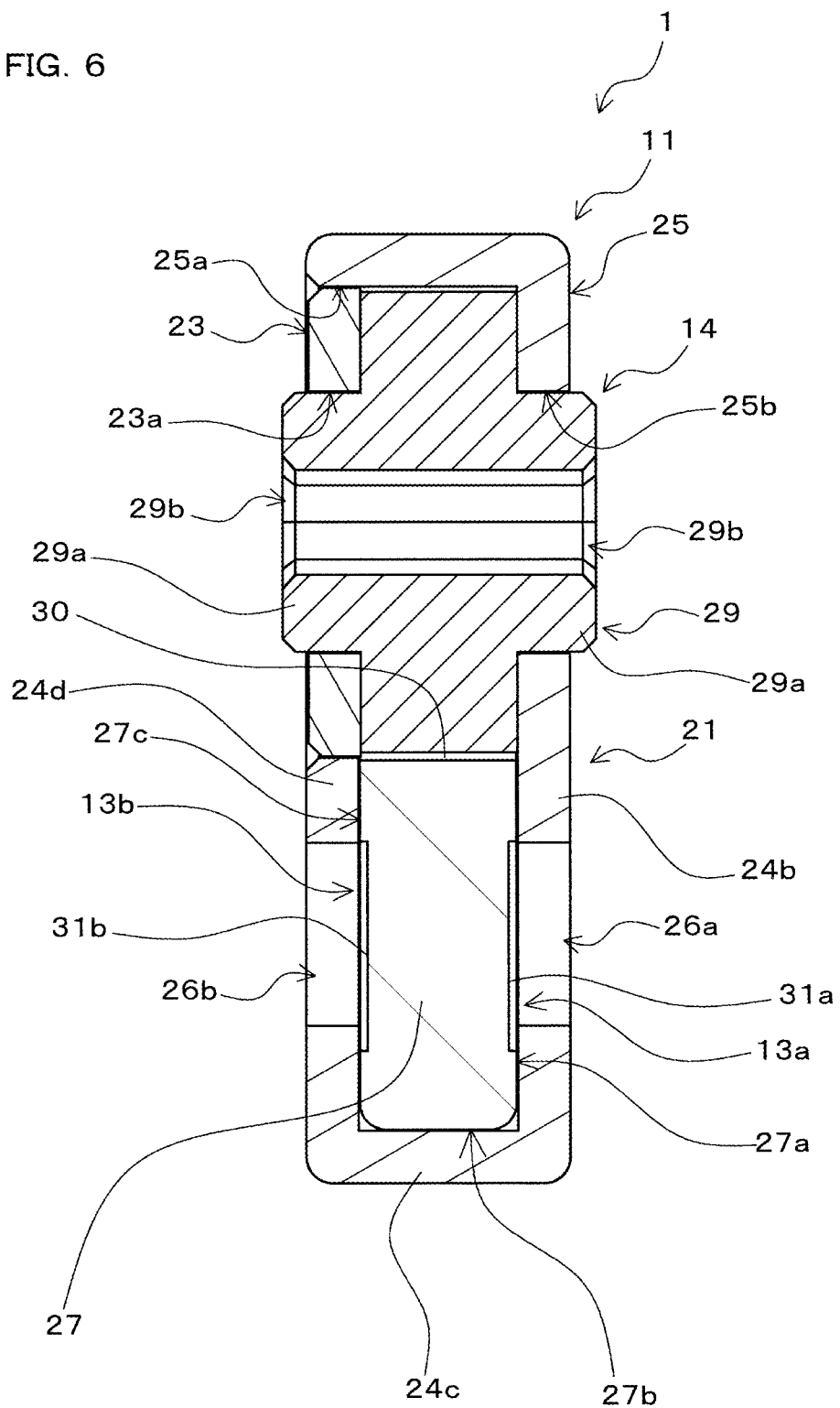
FIG. 6 is a cross-sectional view showing a cross section as viewed from the position of arrows A-A in FIG. 2.

FIG. 6 is a cross-sectional view showing a cross section as viewed from the position of arrows A-A in FIG. 2. The housing 11 shown in FIGS. 1 to 6 is provided so as to be able to be fixed to the tibia 101 or a component attached to the tibia 101. This embodiment describes an exemplary mode of the housing 11 provided so as to be able to be fixed to the tibia 101.

The housing 11 is constituted by a housing body 21, a first bone contact portion 22, and a lid 23. The housing body 21 and the first bone contact portion 22 are formed by a pressing process or a drawing process using a metal plate, for example. The housing body 21 and the first bone contact portion 22 may be formed by a process of joining a plurality of metallic members by means of welding. The housing body 21 and the first bone contact portion 22 may be formed by a process of shaving a metal ingot. The housing body 21 and the first bone contact portion 22 may be formed by appropriately combining the aforementioned processes.

The housing body 21 is provided as a body part of the housing 11. The housing body 21 is provided with a tubular part within which the later-described slider 12 is arranged slidably, and a pinion arrangement portion 25 within which a pinion 29 of the later-described drive mechanism 14 is arranged.

The aforementioned tubular part of the housing body 21 is constituted by four walls (24a, 24b, 24c, and 24d) that form a rectangular cross section. The wall 24a and the wall 24c are provided so as to extend parallel with each other, and the wall 24b and the wall 24d are provided parallel with each other. The wall 24b and the wall 24d are provided so as to extend in a direction perpendicular to the wall 24a and the wall 24c.

The wall 24a is provided with the pinion arrangement portion 25, the wall 24b is provided with a gauge window 26a, and the wall 24d is provided with a gauge window 26b. The gauge windows (26a and 26b) are provided as opening windows that expose a part of gauges (31a and 31b) in the later-described position display portions (13a and 13b) to the outside of the housing body 21. The gauge windows (26a and 26b) are provided as elongated holes extending in a direction in which the tubular part of the housing body 21 extends in a tubular manner, the direction being the longitudinal direction of the walls (24b and 24d). For this reason, the gauge windows (26a and 26b) are configured to be elongated holes extending in a direction in which the slider 12 slides relative to the housing 11.

An opening 21a, which is open to the outside, is provided at one end of the housing body 21 in the longitudinal direction (the direction of the extension in a tubular manner) (see FIGS. 3 to 5). The later-described slider 12 is inserted in the housing 11 from the opening 21a of the housing body 21, and is arranged slidably. Note that an end face extending obliquely from the wall 24a side to the wall 24c side is provided at one end of the housing body 21 at which the opening 21a is provided. The opening 21a is open so as to expand in the aforementioned obliquely extending end face at one end of the housing body 21.

The pinion arrangement portion 25 of the housing body 21 is provided as a part formed so as to rise cylindrically from the wall 24a to the outside. A space in which the pinion 29 in the later-described drive mechanism 14 is arranged is provided within the pinion arrangement portion 25.

The first bone contact portion 22 is provided as a part that comes into contact with and is fixed to the tibia 101, which is the first bone. The first bone contact portion 22 is provided so as to project in a cantilevered manner from the housing body 21. The first bone contact portion 22 is provided so as to project in a cantilevered manner from the wall 24c side at one end of the housing body 21 at which the opening 21a is formed. The first bone contact portion 22 projects and extends in a cantilevered manner from the housing body 21 in a direction perpendicular to the longitudinal direction of the housing body 21. Note that the housing 11 is provided with a first curved portion 22d having a curved surface that gently curves on a corner at the end of the housing body 21 at which the first bone contact portion 22 projects, the corner being on the side opposite to the side where the first bone contact portion 22 projects. Thus, the housing 11 is configured to prevent the corner at the end of the housing body 21 from interfering with the femur 102 when the first bone contact portion 22 is fixed to the tibia 101 and the stability of the state of connection between the tibia 101 and the femur 102 is measured as described later.

The first bone contact portion 22 is provided with a flat contact surface 22a that comes into contact with the tibia 101. Furthermore, the first bone contact portion 22 is provided with a plurality of (in this embodiment, two) through holes (22b and 22c) into which the later-described fixation pins 15 are inserted so as to pass therethrough. The through hole 22b is provided as a hole that passes through the first bone contact portion 22 in a direction parallel with the longitudinal direction of the housing body 21. The through hole 22c is provided as a hole that passes through the first bone contact portion 22 in an oblique direction relative to the direction parallel with the longitudinal direction of the housing body 21.

The lid 23 is provided as a disk-like member in which a pinion support hole 23a, which is a through hole, is provided at the center. The lid 23 is attached and fixed to the housing body 21. Note that the pinion arrangement portion 25 in the housing body 21 is provided with a circular hole 25a that is open on the wall 24d side. The lid 23 is attached to the housing body 21 by being fitted into the hole 25a. Note that the outer-circumferential edge of the lid 23 and the inner-circumferential edge of the hole 25a may be fixed to each other by performing a joining process such as welding at a plurality of points, for example.

The pinion support hole 23a provided at the center of the lid 23 is provided as a hole that rotatably supports the later-described pinion 29. A pinion support hole 25b that rotatably supports the pinion 29 is also provided as a through hole on the wall 24h side in the pinion arrangement portion 25.

Slider

The slider 12 shown in FIGS. 1 to 6 is provided so as to be slidable relative to the housing 11. The slider 12 is provided so as to be able to abut against or be fixed to the femur 102 or a component attached to the femur 102. This embodiment describes an exemplary mode of the slider 12 that is provided so as to be able to abut against the femur 102.

The slider 12 is constituted by a slider body 27 and a second bone contact portion 28. The slider body 27 and the second bone contact portion 28 are formed by a process of joining a plurality of metallic members by means of welding, for example. The slider body 27 and the second bone contact portion 28 may be formed by a pressing process, or a process of shaving a metal ingot. The slider body 27 and the second bone contact portion 28 may be formed by appropriately combining the aforementioned processes.

The slider body 27 is provided as a body part of the slider 12, and is provided, for example, as an elongated, rectangular parallelepiped part that has a substantially rectangular cross section and extends linearly. The slider body 27 is inserted into the housing body 21 of the housing 11 from the opening 21a in the longitudinal direction of the slider body 27. The slider body 27 is slidably arranged within the housing body 21 in the longitudinal direction of the housing body 21.

The slider body 27 is provided with three sliding faces (27a, 27h, and 27c) that extend in the longitudinal direction of the slider body 27. The sliding face 27a and the sliding face 27c are configured to be faces extending parallel with each other. The sliding face 27h is configured to be a face perpendicular to the sliding face 27a and the sliding face 27c. The sliding face 27a, the sliding face 27h, and the sliding face 27c slide inward of the wall 24b, the wall 24c, and the wall 24d, respectively, relative to the housing body 21.

The second bone contact portion 28 is provided as a part that comes into contact with and abuts against the femur 102, which is the second bone. The second bone contact portion 28 is provided with a flat contact surface 28a that comes into contact with the femur 102. The second bone contact portion 28 is provided so as to project in a cantilevered manner from the slider body 27. The second bone contact portion 28 projects and extends in a cantilevered manner from the slider body 27 in a direction perpendicular to the longitudinal direction of the slider body 27.

The second bone contact portion 28 is provided so as to project in a cantilevered manner at an end of the slider body 27 that is exposed to the outside from the housing body 21 in a state where the slider body 27 is inserted in the housing body 21. Furthermore, the second bone contact portion 28 is arranged so as to project to the side opposite to the wall 24c side relative to the housing body 21 in a state where the slider body 27 is inserted in the housing body 21. Note that the slider 12 is provided with a second curved portion 28h having a curved surface that gently curves, on a corner at the end of the slider body 27 at which the second bone contact portion 28 projects, the corner being on the side opposite to the side where the second bone contact portion 28 projects. Thus, the slider 12 is configured to prevent the corner at the end of the slider body 27 from interfering with the tibia 101 when the stability of the state of connection between the tibia 101 and the femur 102 is measured as described later with the second bone contact portion 28 abutting against the femur 102.

With the above configuration, in the measurement instrument for joint surgery 1, the first bone contact portion 22 and the second bone contact portion 28 are provided so as to extend in a cantilevered manner in opposite directions that are parallel with a direction intersecting the sliding direction of the slider 12 relative to the housing 11. Note that this embodiment describes an exemplary mode of the first bone contact portion 22 and the second bone contact portion 28 that extend in a cantilevered manner in opposite directions that are parallel with a direction perpendicular to the sliding direction of the slider 12 relative to the housing 11.

Position Display Portion

The position display portions (13a and 13b) shown in FIGS. 1 to 6 are provided as a mechanism for displaying the position of the slider 12 relative to the housing 11. The position display portion 13a is provided in the wall 24h of the housing 11 and the sliding face 27a of the slider 12. The position display portion 13b is provided in the wall 24d of the housing 11 and the sliding face 27c of the slider 12. The position display portion 13a and the position display portion 13b are configured in a similar manner.

The position display portion 13a is constituted by a gauge 31a and a reading position indicating portion 32a. The gauge 31a is provided in one of the housing 11 and the slider 12. In this embodiment, the gauge 31a is provided in the slider 12. More specifically, the gauge 31a is configured to be a gauge that is marked at even intervals in the sliding face 27a of the slider 12. For example, the gauge 31a is configured to be a plurality of groove-like marks marked at intervals of 1 millimeter in the sliding face 27a. Note that, in the sliding face 27a, values corresponding to respective marks or some of the marks may be marked together with the plurality of marks in the gauge 31a.

The reading position indicating portion 32a is provided in the other one of the housing 11 and the slider 12. In this embodiment, the reading position indicating portion 32a is provided in the housing 11. The reading position indicating portion 32a is provided as a mark indicating a reading position in the gauge 31a. More specifically, the reading position indicating portion 32a is configured to be a groove-like mark marked near the gauge window 26a in the wall 24h of the housing body 21.

When the slider 12 slides relative to the housing 11 in the longitudinal direction of the housing 11, a part of the gauge 31a is always exposed from the gauge window 26a. Upon the slider 12 sliding relative to the housing 11, the plurality of marks in the gauge 31a are relatively displaced with respect to the gauge window 26a and the reading position indicating portion 32a. Therefore, when the slider 12 slides relative to the housing 11, the amount of relative movement of the slider 12 with respect to the housing 11 is ascertained by ascertaining the position of the gauge 31a that corresponds to the position of the reading position indicating portion 32a before and after the sliding.

The position display portion 13b is constituted by a gauge 31b and a reading position indicating portion 32b. The gauge 31b is provided in the slider 12, and is configured to be a gauge marked at equal intervals in the sliding face 27c of the slider 12. For example, the gauge 31b is configured to be a plurality of groove-like marks marked at intervals of 1 millimeter in the sliding face 27c.

The reading position indicating portion 32b is provided in the housing 11, and is provided as a mark indicating a reading position in the gauge 31b. More specifically, the reading position indicating portion 32b is configured to be a groove-like mark marked near the gauge window 26b in the wall 24d of the housing body 21.

When the slider 12 slides relative to the housing 11 in the longitudinal direction of the housing 11, a part of the gauge 31b is always exposed from the gauge window 26b. Upon the slider 12 sliding relative to the housing 11, the plurality of marks in the gauge 31b are relatively displaced with respect to the gauge window 26b and the reading position indicating portion 32b. Therefore, when the slider 12 slides relative to the housing 11, the amount of relative movement of the slider 12 with respect to the housing 11 is ascertained by ascertaining the position of the gauge 31b that corresponds to the position of the reading position indicating portion 32b before and after the sliding.

Drive Mechanism

Figure 7:
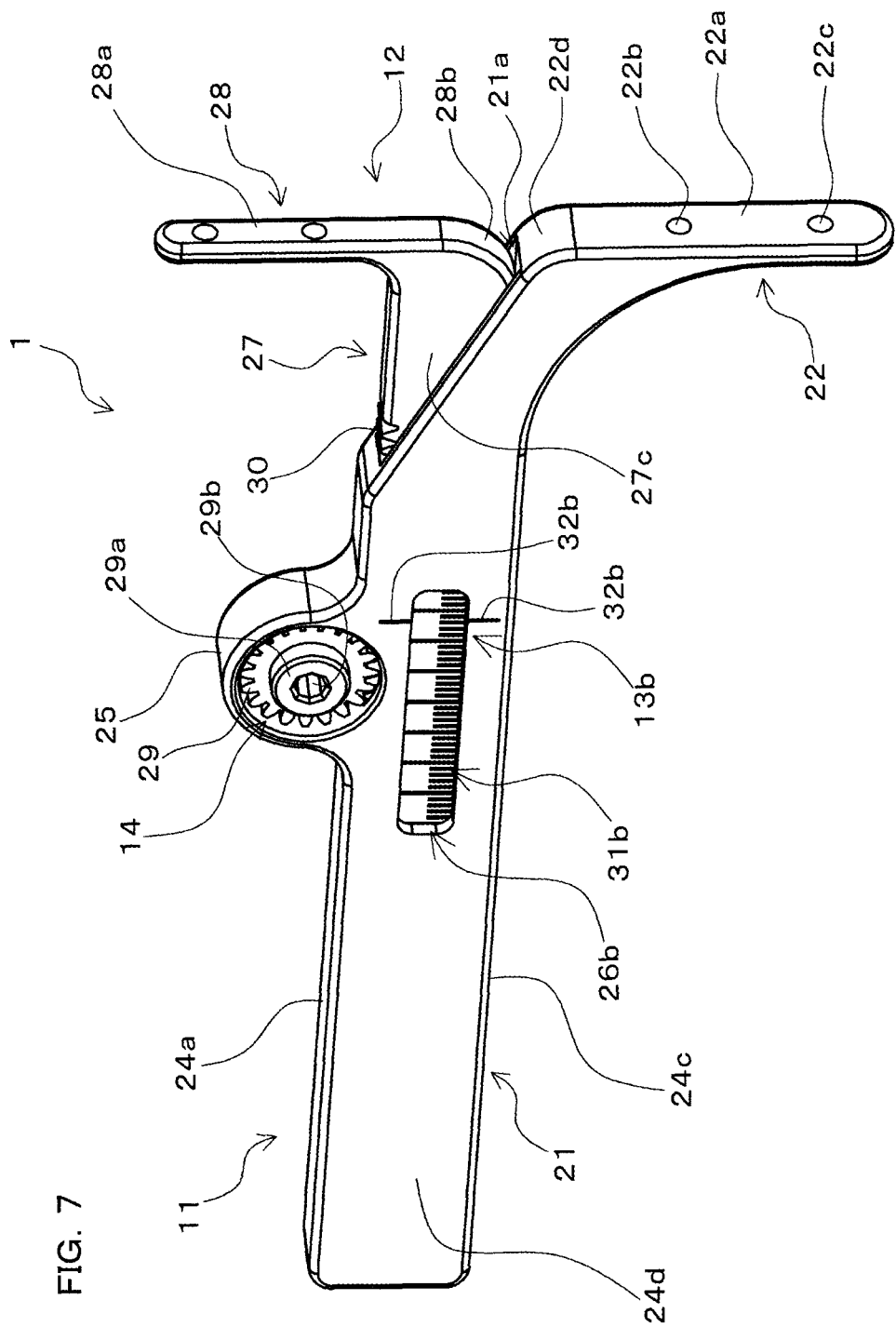
FIG. 7 is a perspective view of the measurement instrument for joint surgery shown in FIG. 4, omitting an element.

FIG. 7 is a perspective view of the measurement instrument for joint surgery 1, omitting an element, i.e. the lid 23. Note that FIG. 7 is a perspective view of the measurement instrument for joint surgery 1 as viewed in the same direction as that in FIG. 4. The drive mechanism 14 shown in FIGS. 1 to 7 is provided as a mechanism that drives the slider 12 so as to slide relative to the housing 11.

In this embodiment, the drive mechanism 14 is provided as a rack-and-pinion mechanism, and is constituted by the pinion 29 and a rack 30. The pinion 29 is constituted by a gear that is provided on its outer circumference, and is provided as a driving force input portion to which a driving force in a rotational direction from the outside is input. The pinion 29 is provided with a shaft 29a at its center part (see FIGS. 3 to 7), and the gear is provided on the outer circumference of the center part of the shaft 29a in the axial direction thereof.

The pinion 29 is attached to the housing 11. The pinion 29 is arranged within the pinion arrangement portion 25 of the housing body 21, and is rotatably supported relative to the housing 11. The pinion 29 is rotatably supported relative to the housing 11 at both ends of the shaft 29a. Specifically, one end of the shaft 29a is inserted in the pinion support hole 25b provided in the pinion arrangement portion 25, and the one end of the shaft 29a is rotatably supported relative to the pinion arrangement portion 25. The other end of the shaft 29a is inserted in the pinion support hole 23a provided in the lid 23, and the other end of the shaft 29a is rotatably supported relative to the lid 23. With the above configuration, the pinion 29 is rotatably supported relative to the housing 11.

Note that, when the pinion 29 is attached to the housing 11, initially, the pinion 29 is arranged within the pinion arrangement portion 25 with the one end of the shaft 29a inserted in the pinion support hole 25b. Then, the lid 23 is attached and fixed to the housing body 21 such that the other end of the shaft 29a is inserted in the pinion support hole 23a.

Figure 8:
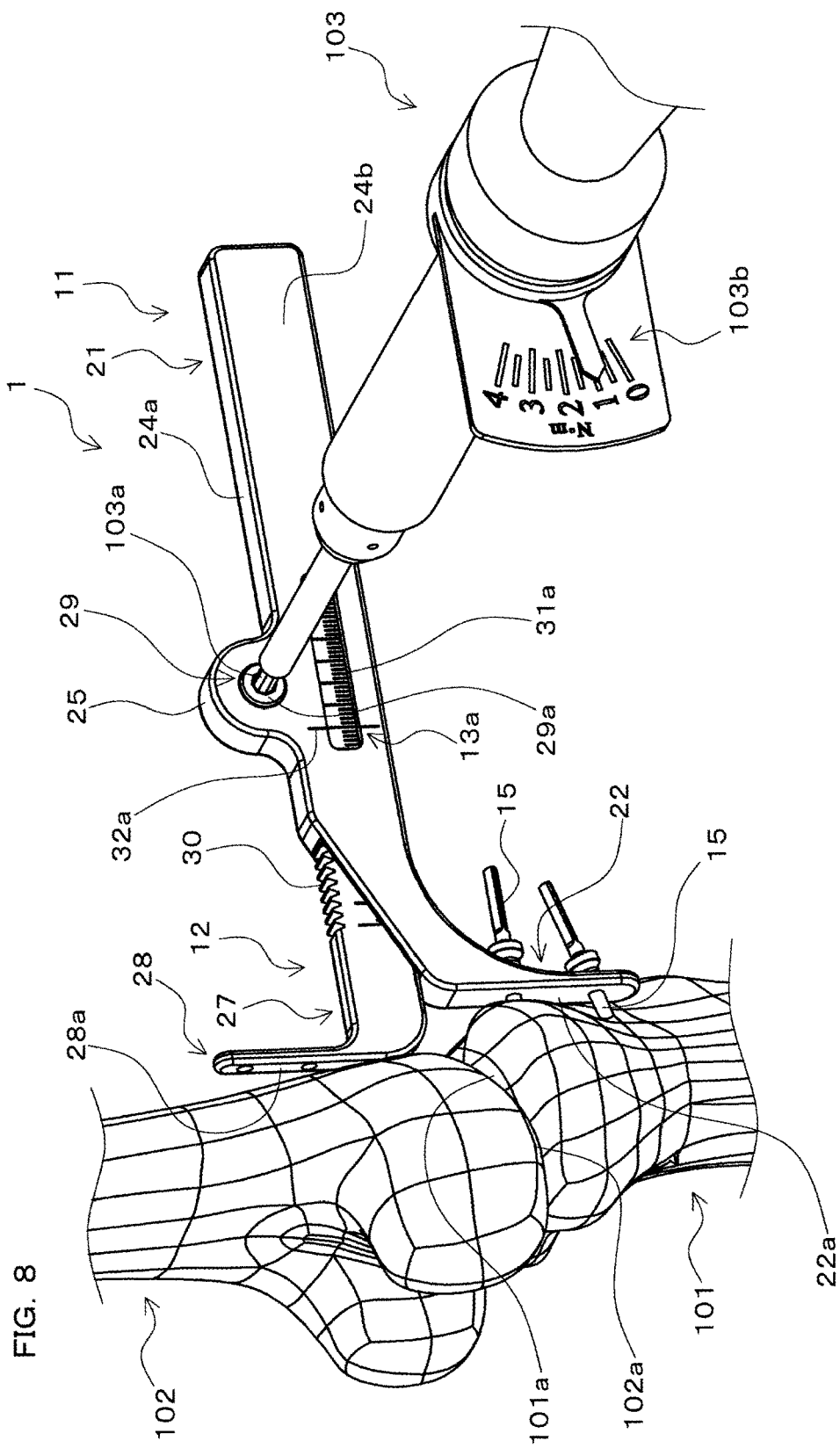
FIG. 8 is an enlarged diagram of a part of FIG. 1.

FIG. 8 is an enlarged diagram of a part of FIG. 1. The shaft 29a of the pinion 29 is provided with a connection hole 29b, which is to be connected to a torque input shaft 103a at a tip of a torque driver 103 serving as a torque generation device for generating a driving force in a rotational direction to be input to the drive mechanism 14 (see FIGS. 3 to 8).

The connection hole 29b is provided as a hole having a polygonal cross section that passes through the shaft 29a in the axial direction. The cross section of the torque input shaft 103a is also formed as a polygonal cross section. The inner-circumferential cross section of the connection hole 29b is formed in a shape corresponding to the cross-sectional shape of the torque input shaft 103a.

When the drive mechanism 14 is to be operated using the driving force of the torque driver 103, initially, the torque input shaft 103a at the tip of the torque driver 103 is inserted into the connection hole 29b. Thus, the torque input shaft 103a is fitted into the connection hole 29b, and the connection hole 29b of the pinion 29 and the torque input shaft 103a of the torque driver 103 are connected. As a result of the torque driver 103 being operated with the torque input shaft 103a of the torque driver 103 inserted, a rotational driving force from the torque driver 103 is input to the pinion 29 that is connected to the torque input shaft 103a.

The rack 30 shown in FIGS. 2 to 8 is provide in the slider body 27 of the slider 12, and is provided as linearly arrayed teeth that mesh with the gear of the pinion 29. The rack 30 is provided as a sliding drive portion that converts the driving force in the rotational direction that is input from the torque driver 103 to the pinion 29 into a driving force in a linear direction, and slides the slider 12 relative to the housing 11.

The rack 30 is arranged so as to oppose the wall 24a in a state where the slider body 27 is arranged within the housing body 21. A part of an inner circumferential wall that demarcates the space within the pinion arrangement portion 25 in the housing body 21 is open to the space where the slider 12 is arranged inside the tubular part of the housing body 21. The gear of the pinion 29 and the linear teeth of the rack 30 mesh with each other via the aforementioned opening provided in the inner-circumferential wall of the pinion arrangement portion 25.

Upon the rotational driving force from the torque driver 103 being input to the pinion 29, the pinion 29 that is rotatably supported by the housing 11 rotates. With the rotation of the pinion 29, the rack 30 that meshes with the pinion 29 moves together with the slider 12 in the longitudinal direction of the housing 11. Thus, the slider 12 slides relative to the housing 11 in the longitudinal direction of the housing 11.

Figure 9:
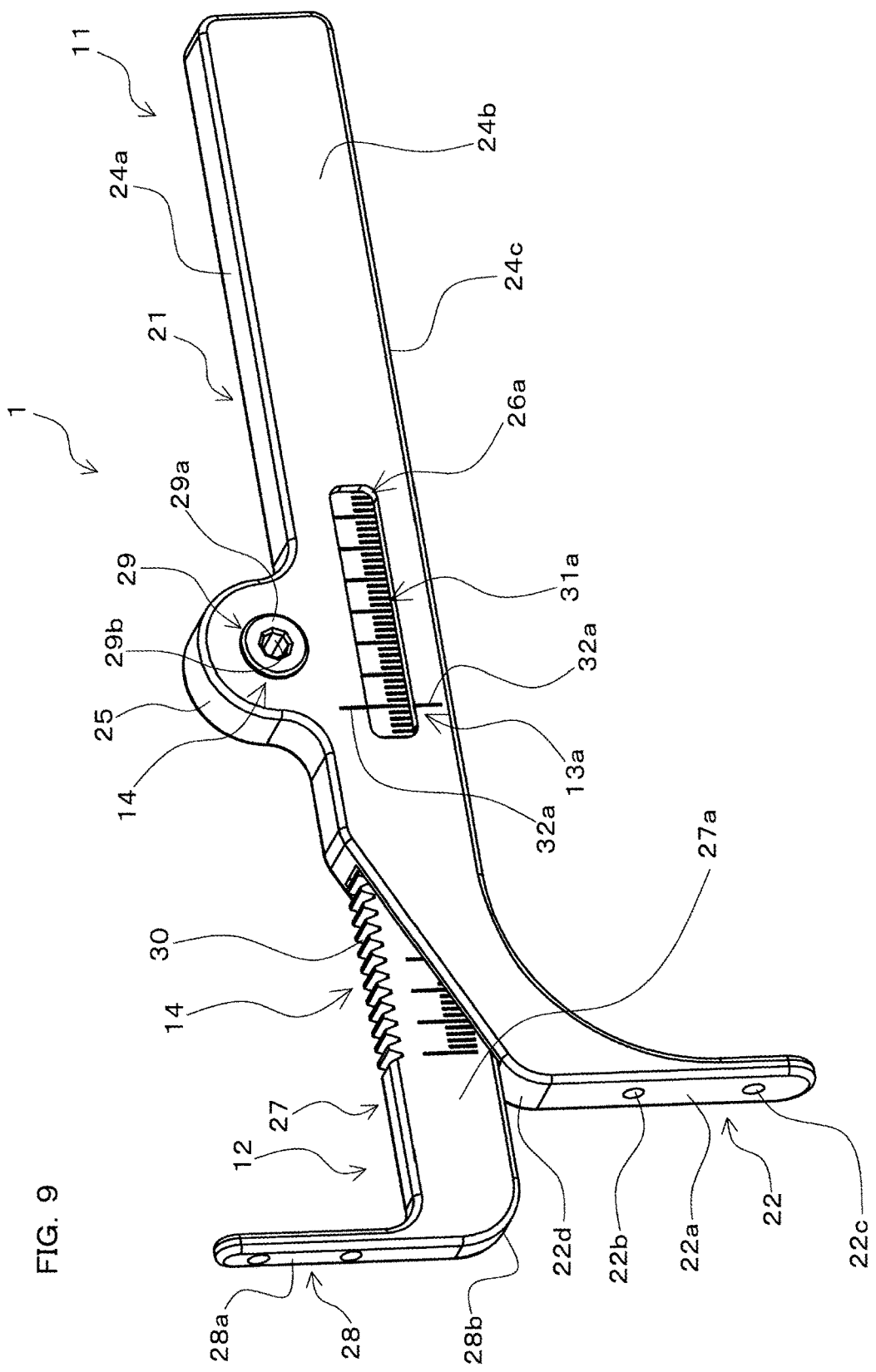
FIG. 9 is a perspective view of the measurement instrument for joint surgery shown in FIG. 3, with the position of a slider relative to a housing different from that in FIG. 3.
Figure 10:
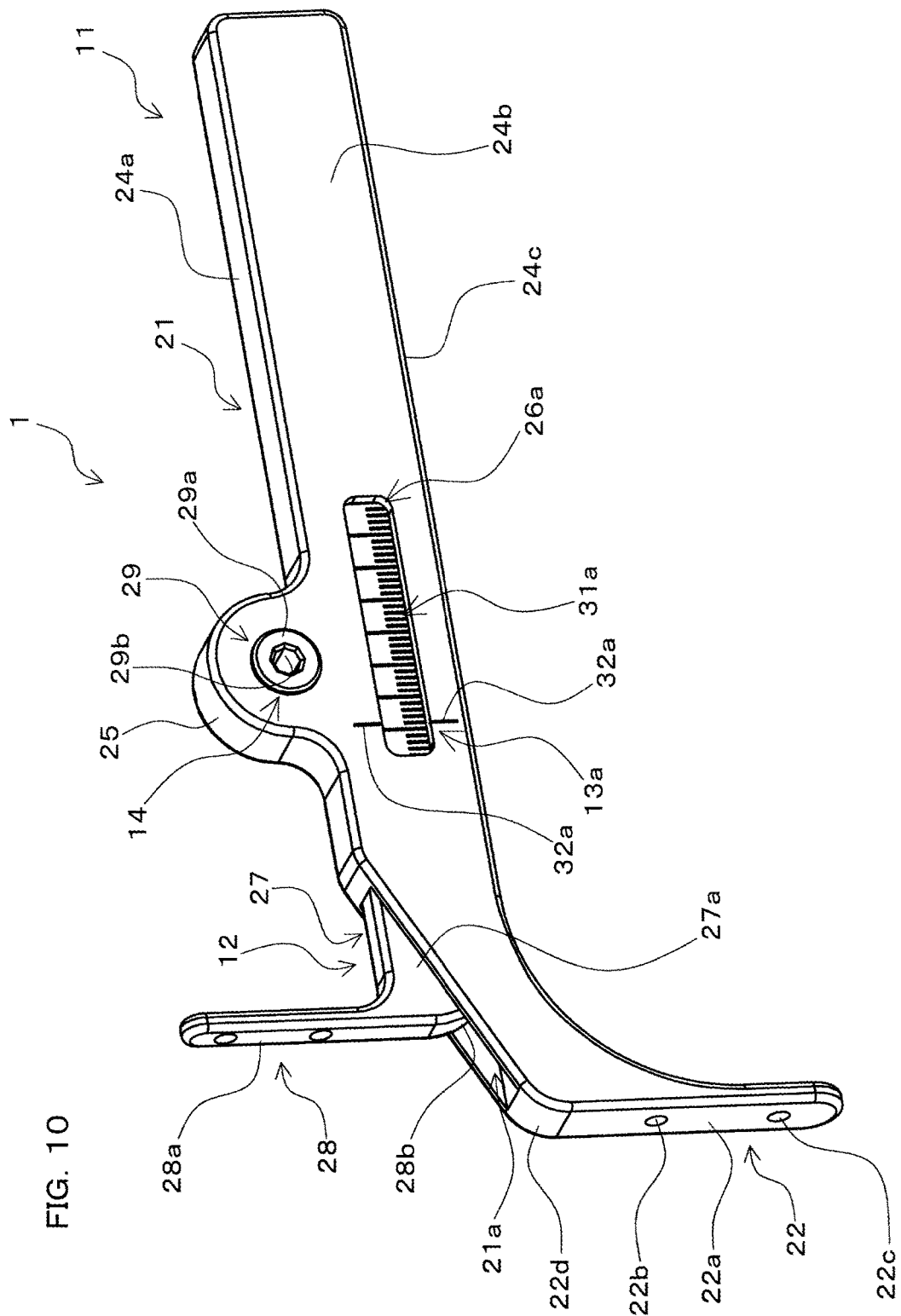
FIG. 10 is a perspective view of the measurement instrument for joint surgery shown in FIG. 3, with the position of the slider relative to the housing different from that in FIG. 3.

Note that FIGS. 9 and 10 are perspective views of the measurement instrument for joint surgery 1, with the position of the slider 12 relative to the housing 11 different from that in FIG. 3. FIG. 9 shows a state where the slider 12 has moved so as to be further projected relative to the housing 11 from the state shown in FIG. 3. On the other hand, FIG. 10 shows a state where the slider 12 has moved so as to be further withdrawn relative to the housing 11 toward the distal side within the housing body 21 from the state shown in FIG. 3. As shown in FIGS. 9 and 10, the drive mechanism 14 is configured to enable the slider 12 to slide relative to the housing 11 between a withdrawn state and a projecting state in accordance with the rotational direction of the pinion 29, as a result of the rotational driving force being input from the torque driver 103.

Fixation Pin

The fixation pins 15 shown in FIGS. 1, 2, and 8 are used together with the measurement instrument for joint surgery 1. The fixation pins 15 are used as fixation members for fixing the housing 11 to the tibia 101, which is the first bone. This embodiment describes an exemplary mode in which a plurality of (two) fixation pins 15 are used. One of the fixation pins 15 engages with the tibia 101 in a state of being inserted in the through hole 22b in the housing 11, and fixes the housing 11 to the tibia 101. The other fixation pin 15 engages with the tibia 101 in a state of being inserted in the through hole 22c in the housing 11, and fixes the housing 11 to the tibia 101.

The fixation pins 15 are each provided with an engaging portion 15a that engages with the tibia 101, and a stopper portion 15b that is locked to the housing 11. The engaging portion 15a is provided as a linearly extending part that is to be inserted into the through hole (22b and 22c) in the housing 11. The tip part of the engaging portion 15a is provided as a pointed part so as to be able to engage with the tibia 101 as a result of being stuck into the tibia 101.

The stopper portion 15b is provided as a part that expands in a flange-like manner in a radial direction relative to the shaft part of the linear engaging portion 15a. When the engaging portion 15a is inserted in the through hole (22b and 22c) in the housing 11, the fixation pin 15 abuts, at the stopper portion 15b, against the edge of the through hole (22b and 22c). Thus, the fixation pin 15 is locked at the stopper portion 15b relative to the housing 11.

Note that this embodiment has described an exemplary mode of the fixation pins 15 that serve as fixing members for fixing the housing 11 to the tibia 101. However, this need not be the case. For example, a fixation screw having an external thread that is to engage with the tibia 101 may be used as a fixing member for fixing the housing 11 to the tibia 101.

Operation of Measurement Instrument for Joint Surgery

Next, the operation of the measurement instrument for joint surgery 1 will be described. The measurement instrument for joint surgery 1 is used in knee joint surgery in a state where an incision is made in a part of the skin near the knee joint and a part of the knee joint is exposed to the outside. As shown in FIG. 8, initially, the measurement instrument for joint surgery 1 is arranged such that the first bone contact portion 22 of the housing 11 is in a state of abutting against the end of the tibia 101 on the proximal side from the anterior face side of a patient.

In the above state, the fixation pins 15 are inserted into the through holes (22b and 22c) of the housing 11, and are hammered into the tibia 101. Then, the fixation pins 15 enter a state of being stuck into and engaging with the tibia 101 while being locked to the housing 11. Thus, the housing 11 is fixed to the tibia 101 at the first bone contact portion 22.

Note that, since a plurality of (two in this embodiment) fixation pins 15 are provided, the housing 11 can be stably fixed to the tibia 101 at a plurality of portions. The two through holes (22b and 22c) provided in the housing 11 are provided so as to extend in directions that are not parallel with each other. For this reason, the two fixation pins 15 inserted in the through holes (22b and 22c) stick to and engage with the tibia 101 in directions that are not parallel with each other. Thus, the housing 11 can be further stably fixed to the tibia 101.

After the housing 11 is fixed to the tibia 101, next, the torque input shaft 103a of the torque driver 103 is connected to the connection hole 29b in the pinion 29. A surgeon who is performing the joint surgery operates the torque driver 103 to input the rotational driving force to the pinion 29 and operate the drive mechanism 14, and slides the slider 12 relative to the housing 11 up to the position where the slider comes into contact with the end of the femur 102 on the distal side. At this time, the slider 12 comes into contact, at the second bone contact portion 28, with the end of the femur 102 on the distal side, on the anterior face side of the patient. In the above operation of moving the slider 12 up to the position where the slider 12 comes into contact with the end of the femur 102, the second bone contact portion 28 is caused to lightly come into contact with the end of the femur 102 to the extent that the femur 102 is not relatively moved with respect to the tibia 101, and the movement of the slider 12 relative to the housing 11 is temporarily stopped.

In a state where the slider 12 is lightly in contact with the anterior face side of the end of the femur 102 as described above, the position of the slider 12 relative to the housing 11 is read using the position display portion 13a by the surgeon. That is to say, the position of the mark indicated in the gauge 31a by the reading position indicating portion 32a is read.

Note that, the above description based on FIG. 8 takes, as an example, the case where the torque input shaft 103a of the torque driver 103 is inserted in the connection hole 29b in the pinion 29 from the wall 24h side of the housing 11. Furthermore, the above description takes, as an example, the mode in which the position of the slider 12 relative to the housing 11 is read using the position display portion 13a. However, this need not be the case. A mode may be implemented in which the torque input shaft 103a is inserted into the connection hole 29b in the pinion 29 from the wall 24d side of the housing 11 (i.e. the lid 23 side). Also, a mode may be implemented in which the position of the slider 12 relative to the housing 11 is read using the position display portion 13b.

As mentioned above, after reading the position of the slider 12 relative to the housing 11 in a state where the slider 12 is lightly in contact with the anterior face side of the end of the femur 102, next, the torque driver 103 is further operated by the surgeon. That is to say, the surgeon operates the torque driver 103 to input the rotational driving force to the pinion 29 and operate the drive mechanism 14, and further slides the slider 12 relative to the housing 11.

When the torque driver 103 is operated as described above, the first bone contact portion 22 of the housing 11 is fixed to the anterior face side of the end of the tibia 101 on the proximal side, and the second bone contact portion 28 of the slider 12 abuts against the anterior face side of the end of the femur 102 on the distal side. Then, the housing 11 and the slider 12 are arranged in a state where the longitudinal direction of the housing body 21 and the slider body 27 extends in the anterior-posterior direction of the patient.

As a result of the above, after the torque driver 103 is operated and the drive mechanism 14 operates, the drive mechanism 14 drives the slider 12 so as to slide relative to the housing 11 in the anterior-posterior direction of the patient. More specifically, the drive mechanism 14 drives the slider 12 so as to slide the slider 12 relative to the housing 11 in the direction from the anterior face side to the posterior face side of the patient. Thus, the measurement instrument for joint surgery 1 is configured to relatively move the femur 102, which is the second bone, relative to the tibia 101, which is the first bone, in the anterior-posterior direction along joint faces (101a and 102a) between the tibia 101 and the femur 102, as a result of the slider 12 sliding relative to the housing 11. Note that the joint face 101a is a joint face at the end of the tibia 101 on the proximal side, and the joint face 102a is a joint face at the end of the femur 102 on the distal side.

With the measurement instrument for joint surgery 1, the surgeon relatively moves the end of the femur 102 with respect to the end of the tibia 101 along the joint faces in the anterior-posterior direction as described above, and checks the stability of the state of connection between the tibia 101 and the femur 102 that are connected by soft tissue such as ligaments. Then, the surgeon stops operating the torque driver 103 after having moved the femur 102 relative to the tibia 101 to the extent required for checking the stability of the state of connection between the tibia 101 and the femur 102. Then, in this state, the position of the slider 12 relative to the housing 11 is read using the position display portion 13a by the surgeon. That is to say, the position of the mark indicated in the gauge 31a by the reading position indicating portion 32a is read.

As described above, when the stability of the state of connection between the tibia 101 and the femur 102 is checked, initially, the position of the slider 12 relative to the housing 11 in a state where the slider 12 is lightly in contact with the anterior face side of the end of the femur 102 is read. Next, with the measurement instrument for joint surgery 1, the position of the slider 12 relative to the housing 11 is read in a state where the femur 102 has moved relative to the tibia 101 to the extent required for checking the stability of the state of connection between the tibia 101 and the femur 102. Then, the amount of relative movement when the femur 102 relatively moves with respect to the tibia 101 along the joint faces (101a and 102a) is measured as a difference between the first-read position of the slider 12 relative to the housing 11 and the latter-read position of the slider 12 relative to the housing 11. Thus, with the measurement instrument for joint surgery 1, the stability of the state of connection between the tibia 101 and the femur 102 is measured based on the position of the slider 12 relative to the housing 11 displayed by the position display portion 13a.

In a state where the femur 102 has moved relative to the tibia 101 to the extent required for checking the stability of the state of connection between the tibia 101 and the femur 102, the magnitude of the torque that is input by the torque driver 103 is displayed by a torque display portion 103b in the torque driver 103. Thus, as a result of the torque driver 103 being used, the torque that is input by the torque driver 103 is also measured.

Effects of Measurement Instrument for Joint Surgery

As described above, according to this embodiment, the housing 11 is fixed to the tibia 101. Meanwhile, the slider 12 is arranged in a state of abutting against the femur 102. In this state, the measurement instrument for joint surgery 1 is operated such that the slider 12 slides relative to the housing 11. Thus, the femur 102 is relatively moved with respect to the tibia 101 along the joint faces (101a and 102a). Then, the amount of relative movement when the femur 102 relatively moves with respect to the tibia 101 along the joint faces (101a and 102a) is measured based on the position of the slider 12 relative to the housing 11 displayed by the position display portions (13a and 13b). Thus, with this measurement instrument for joint surgery 1, the tibia 101 and the femur 102 that are connected by soft tissue at a joint are relatively moved along the joint faces (101a and 102a) between these bones, and the stability of the state of connection between these bones is measured as the amount of relative movement in the direction along these joint faces (101a and 102a). That is to say, with this measurement instrument for joint surgery 1, it is possible to relatively move the tibia 101 and the femur 102 in directions other than directions in which these bones are separated from each other, and measure the stability of the state of connection between these bones.

As described above, this embodiment can provide the measurement instrument for joint surgery 1 that can relatively move the tibia 101 and the femur 102 that are connected by soft tissue at a joint, in directions other than directions in which these bones are separated from each other, and measure the stability of the state of connection between these bones.

Also, according to this embodiment, the first bone contact portion 22 and the second bone contact portion 28 extend in a cantilevered manner in opposite directions that are parallel with a direction intersecting the sliding direction of the slider 12 relative to the housing 11. For this reason, a mechanism that relatively moves the femur 102 relative to the tibia 101 along the joint faces (101a and 102a) by the slider 12 sliding relative to the housing 11 can be achieved with a simple structure that includes the first and second bone contact portions (22 and 28) that project in a cantilevered manner respectively from the housing 11 and the slider 12.

Also, according to this embodiment, the position display portions (13a and 13b) that display the position of the slider 12 relative to the housing 11 can be achieved with a simple structure in which the gauges (31a and 31b) are provided in one of the housing 11 and the slider 12 and the reading position indicating portions (32a and 32b) are provided in the other one of the housing 11 and the slider 12.

Also, according to this embodiment, the slider 12 is slid relative to the housing 11 via the drive mechanism 14. Therefore, the slider 12 can be relatively moved with respect to the housing 11 in a smooth and accurate manner. For this reason, the femur 102 can be relatively moved with respect to the tibia 101 along the joint faces (101a and 102a) in a smooth and accurate manner.

Also, according to this embodiment, upon a driving force in a rotational direction from the outside being input, this driving force in the rotational direction is converted into a driving force in a linear direction, and the slider 12 slides relative to the housing 11. For this reason, the slider 12 can be relatively moved with respect to the housing 11 in a smooth and accurate manner using the torque driver 103 that generates the driving force in the rotational direction. Furthermore, since the torque driver 103 can be used, the torque that is input by the torque driver 103 can be measured by the torque driver 103. Thus, in relation to the measurement of the stability of the state of connection between the tibia 101 and the femur 102 in directions other than direction in which these bones are separated from each other, a tensile force generated by soft tissue that connects these bones can also be readily measured.

Also, according to this embodiment, since the first curved portion 22d is provided in the housing 11, it is possible to prevent the corner of the first bone contact portion 22 of the housing 11 on the side opposite to the projecting side from coming into contact and interfering with the femur 102. In addition, since the second curved portion 28b is provided in the slider 12, it is possible to prevent the corner of the second bone contact portion 28 of the slider 12 on the side opposite to the projecting side from coming into contact and interfering with the tibia 101. Accordingly, when the femur 102 is relatively moved with respect to the tibia 101 along the joint faces (101a and 102a) by the measurement instrument for joint surgery 1, or when the angle of the knee joint is changed in a state where the measurement instrument for joint surgery 1 is arranged near the knee joint that is constituted by the end of the tibia 101 and the end of the femur 102, it is possible to prevent the tibia 101 and the femur 102 from interfering with the measurement instrument for joint surgery 1 due to contact therebetween that is not intended by the surgeon.

Second Embodiment

Overview of Measurement Instrument for Joint Surgery

Figure 11:
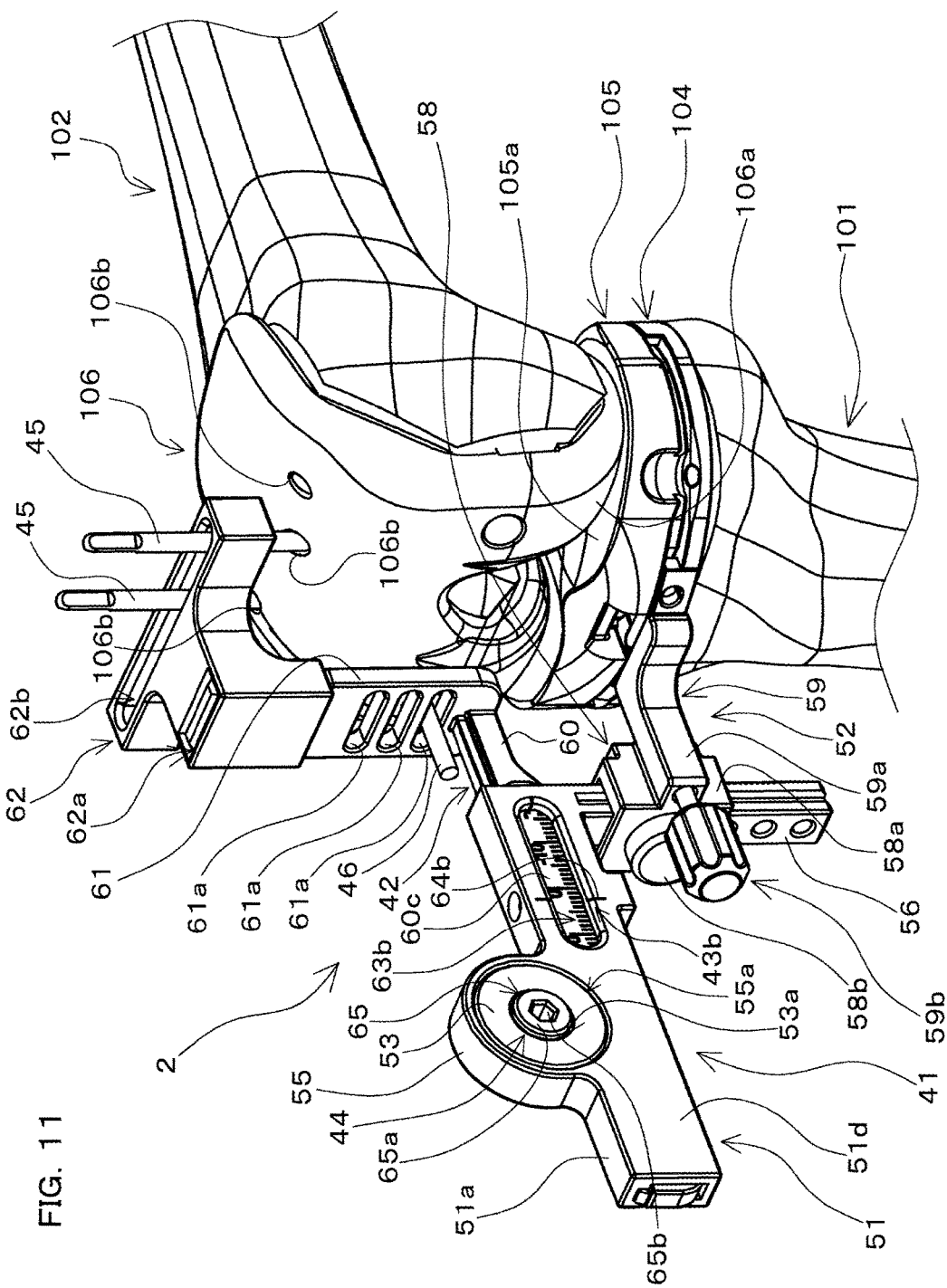
FIG. 11 is a schematic view showing a form of use of a measurement instrument for joint surgery according to a second embodiment of the present invention.
Figure 12:
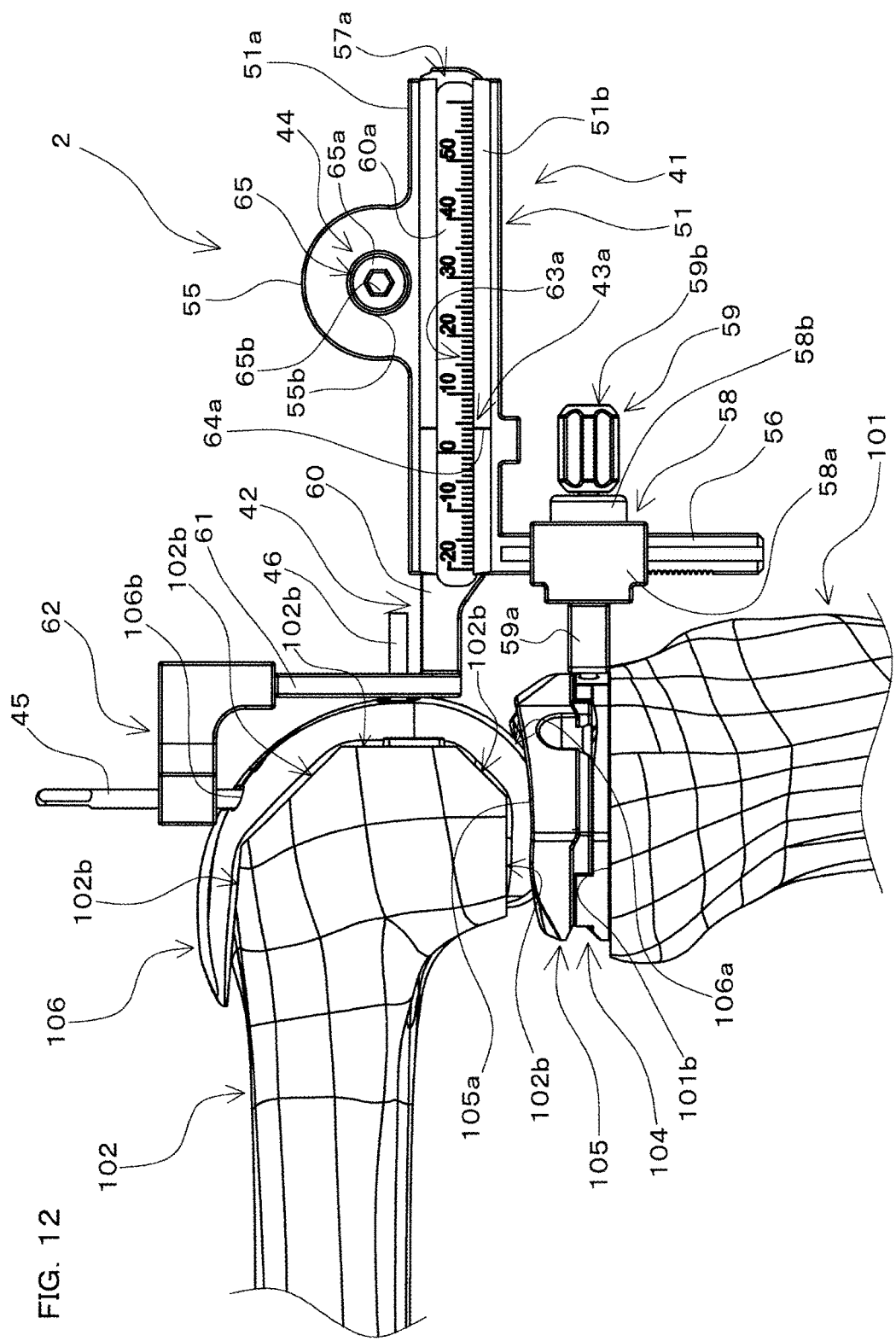
FIG. 12 is a schematic view of the measurement instrument for joint surgery shown in FIG. 11 and the periphery thereof as viewed from a side of the knee joint.
Figure 13:
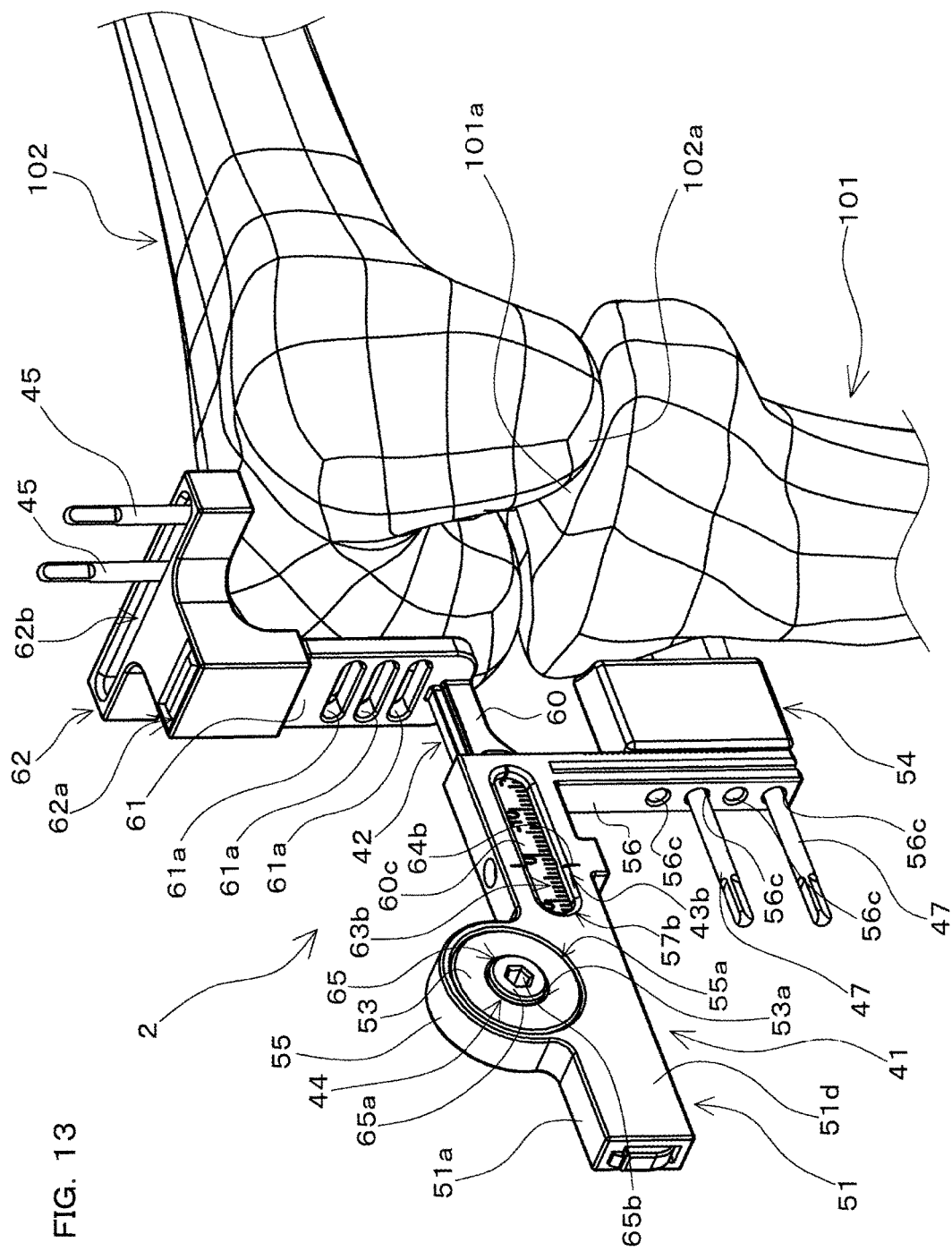
FIG. 13 is a schematic view showing another form of use of the measurement instrument for joint surgery shown in FIG. 11.

Next, a measurement instrument for joint surgery 2 according to a second embodiment of the present invention will be described. FIG. 11 is a schematic view showing a form of use of the measurement instrument for joint surgery 2 according to the second embodiment of the present invention. FIG. 12 is a schematic view of the measurement instrument for joint surgery 2 shown in FIG. 11 and the periphery thereof as viewed from a side of the knee joint. FIG. 13 is a schematic view showing another form of use of the measurement instrument for joint surgery 2.

Similar to the measurement instrument for joint surgery 1 according to the first embodiment, the measurement instrument for joint surgery 2 shown in FIGS. 11 to 13 can be used in various kinds of joint surgery, and can also be used when a joint is in an angle state of either an extension position or a bending position. Note that this embodiment will be described, taking, as an example, a mode in which the measurement instrument for joint surgery 2 is used in artificial knee joint replacement surgery by which a knee joint is replaced with an artificial knee joint. Although this embodiment will be described, taking, as an example, a mode used when the joint knee is at a bending position, the measurement instrument for joint surgery 2 can also be used when the knee joint is at an extension position.

The measurement instrument for joint surgery 2 is used in artificial knee joint replacement surgery, for example, and is provided as an instrument for measuring the stability (lability) of a state of connection between the tibia 101 and the femur 102 that are connected by soft tissue such as ligaments, at a knee joint. The tibia 101 serves as a first bone in this embodiment, and the femur 102 serves as a second bone in this embodiment. Note that the schematic views in FIGS. 11 to 13 omit human tissue other than the tibia 101 and the femur 102. The schematic views in FIGS. 11 to 13 show the tibia 101 and the femur 102 only in the region of the knee joint and the peripheral region.

FIGS. 11 and 12 show a state where components are attached to the tibia 101 that is the first bone and the femur 102 that is the second bone. Specifically, in FIGS. 11 and 12, a tibial tray trial 104 and a tibial insertion trial 105, which serve as components according to this embodiment, are attached to the tibia 101. A femur trial 106, which serves as a component according to this embodiment, is attached to the femur 102. On the other hand, FIG. 13 shows a state where no component is attached to the tibia 101 and the femur 102. The measurement instrument for joint surgery 2 can be used in both states where the components are attached to the tibia 101 and the femur 102 and not attached thereto.

The measurement instrument for joint surgery 2 shown in FIGS. 11 to 13 is constituted by a housing 41, a slider 42, position display portions (43a and 43b), a drive mechanism 44, and the like. Note that FIGS. 11 to 13 also show slider fixation pins 45, a bending position holding pin 46, and housing fixation pins 47, which are used together with the measurement instrument for joint surgery 2. Note that the constituent elements of the measurement instrument for joint surgery 2, such as the housing 41, the slider 42, and the drive mechanism 44, are made of a metallic material such as stainless steel, for example.

Components

Here, a description will be given of the tibial tray trial 104, the tibial insertion trial 105, and the femur trial 106, which serve as the components to be attached to the tibia 101 that is the first bone and the femur 102 that is the second bone.

The tibial tray trial 104 and the tibia insertion trial 105 are formed in a shape that is substantially similar to an implant (not shown) on the tibia side of the artificial knee joint. The tibial tray trial 104 is made of a metallic material such as stainless steel, for example. The tibial insertion trial 105 is made of a resin material, for example.

The tibial tray trial 104 and the tibial insertion trial 105 are temporarily installed on the tibia 101 before the tibia-side implant is attached to the tibia 101 during artificial knee joint replacement surgery. The surgeon checks, in advance, an installation state of the tibia-side implant before installation thereof by temporarily installing the tibial tray trial 104 and the tibial insertion trial 105 onto the tibia 101 during artificial knee joint replacement surgery.

Note that the tibial tray trial 104 is installed at an end of the tibia 101 on the proximal side. At the end of the tibia 101 on the proximal side is provided an excision face 101b, which is formed by being excised along a face substantially perpendicular to the bone axis of the tibia 101. The tibial tray trial 104 is fixed to the excision face 101b and is installed at the end of the tibia 101 on the proximal side. The tibial insertion trial 105 is fixed to and installed on the tibial tray trial 104 installed on the tibia 101. A joint face 105a, which can slide relative to the femur trial 106, is provided on a surface of the tibial insertion trial 105 on the side opposite to the side where the tibial insertion trial 105 is installed on the tibial tray trial 104 (i.e. a surface on the proximal side).

The femur trial 106 is formed in a shape that is substantially similar to a femur-side implant (not shown) of the artificial knee joint. The femur trial 106 is made of a metallic material such as stainless steel, for example. The femur trial 106 is temporarily installed on the femur 102 before the femur-side implant is attached to the femur 102 during the artificial knee joint replacement surgery. The surgeon checks, in advance, the installation state of the femur-side implant before the installation thereof by temporarily installing the femur trial 106 onto the femur 102 during the artificial knee joint replacement surgery.

Note that the femur trial 106 is installed at an end of the femur 102 on the distal side. The end of the femur 102 on the distal side is provided with five excision faces 102b, which are formed by a part of the end of the femur 102 being excised and have different angles. The femur trial 106 is fixed to the excision faces 102b, and is installed at the end of the femur 102 on the distal side. A joint face 106a, which can slide relative to the tibial insertion trial 105, is provided on a surface of the femur trial 106 on the side opposite to the side where the femur trial 106 is installed on the femur 102 (i.e. a surface on the distal side).

Housing

Figure 14:
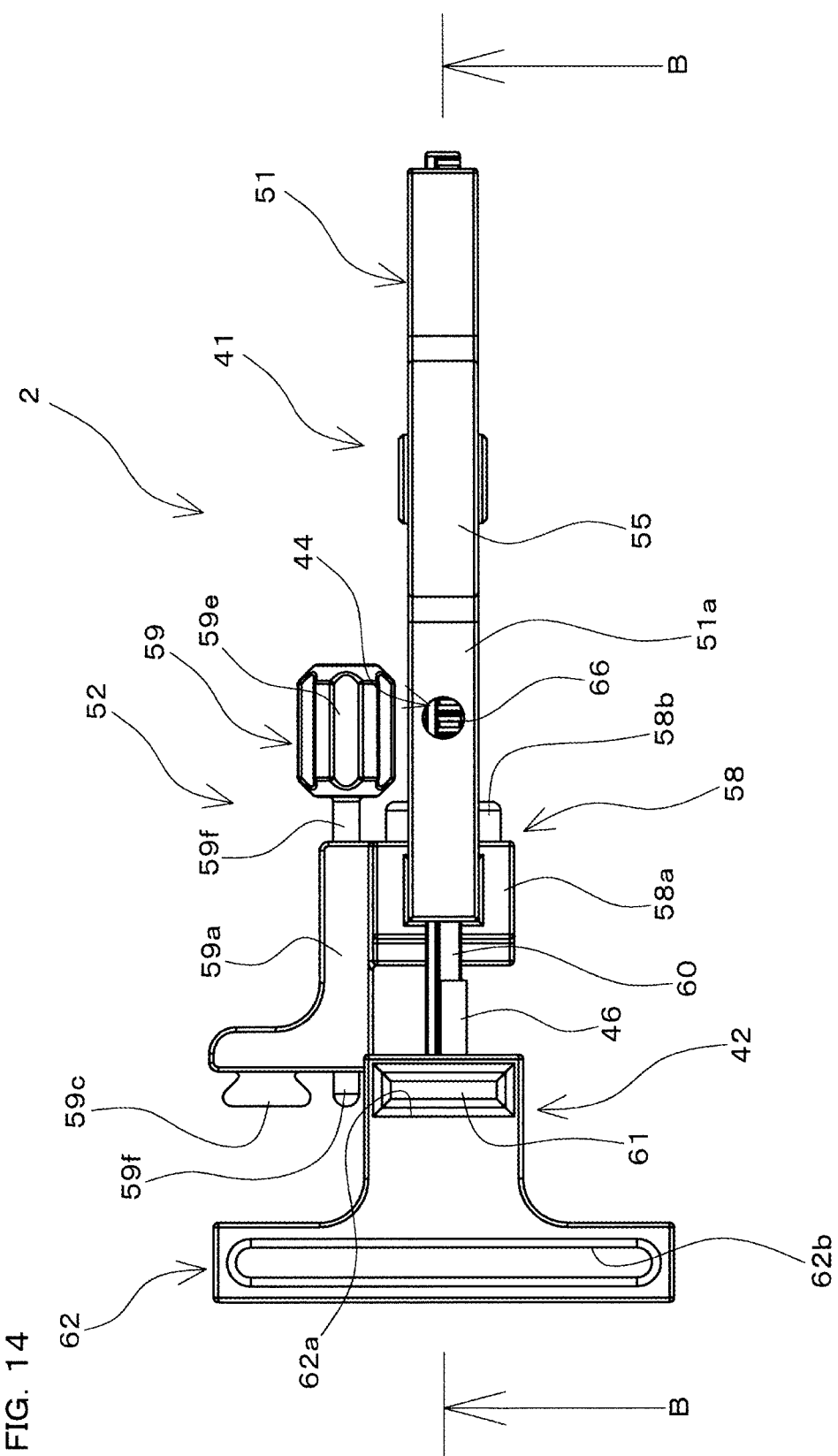
FIG. 14 is a plan view of the measurement instrument for joint surgery shown in FIG. 11.
Figure 15:
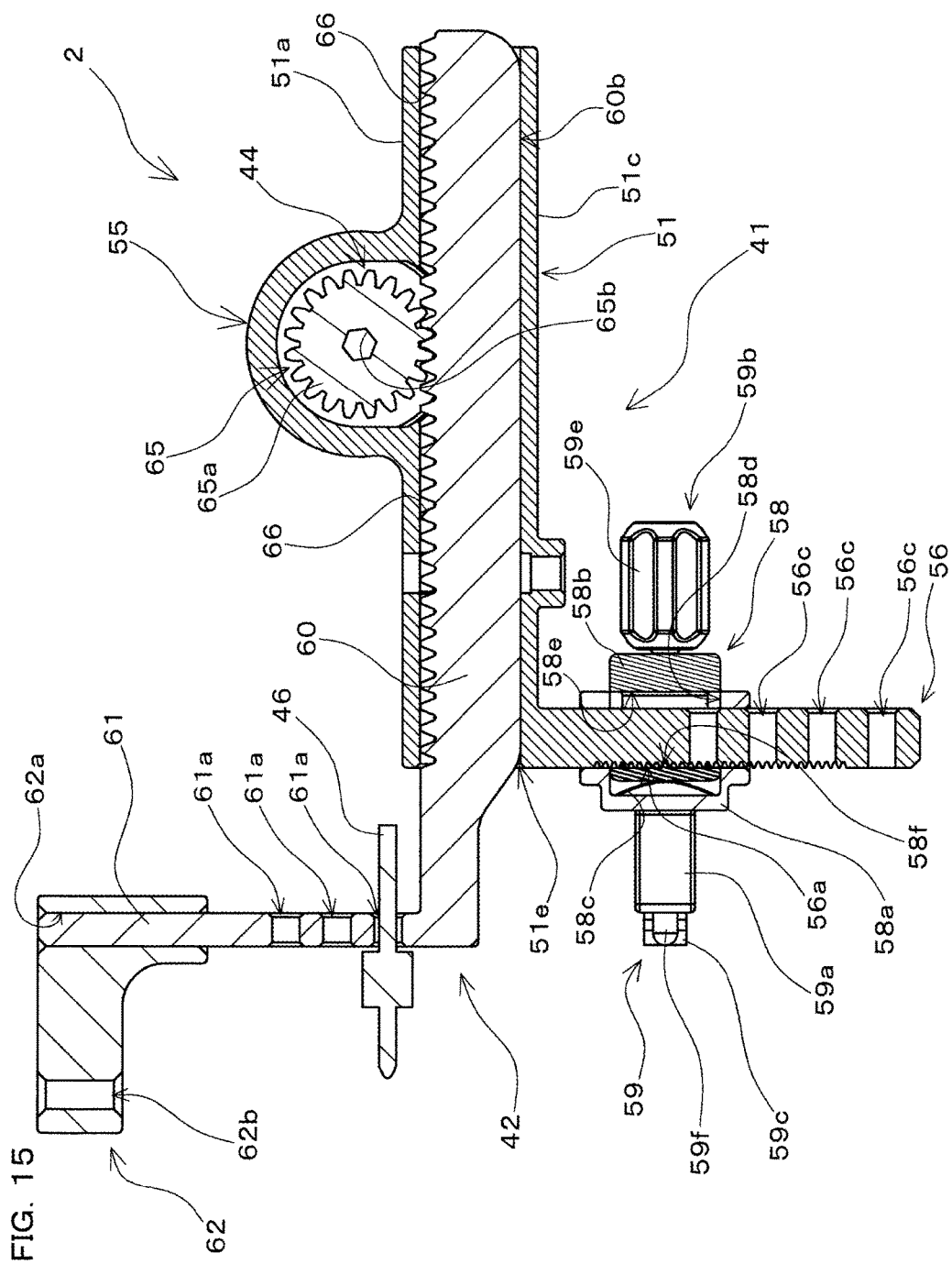
FIG. 15 is a cross-sectional view showing a cross section as viewed from the position of arrows B-B in FIG. 14.
Figure 16:
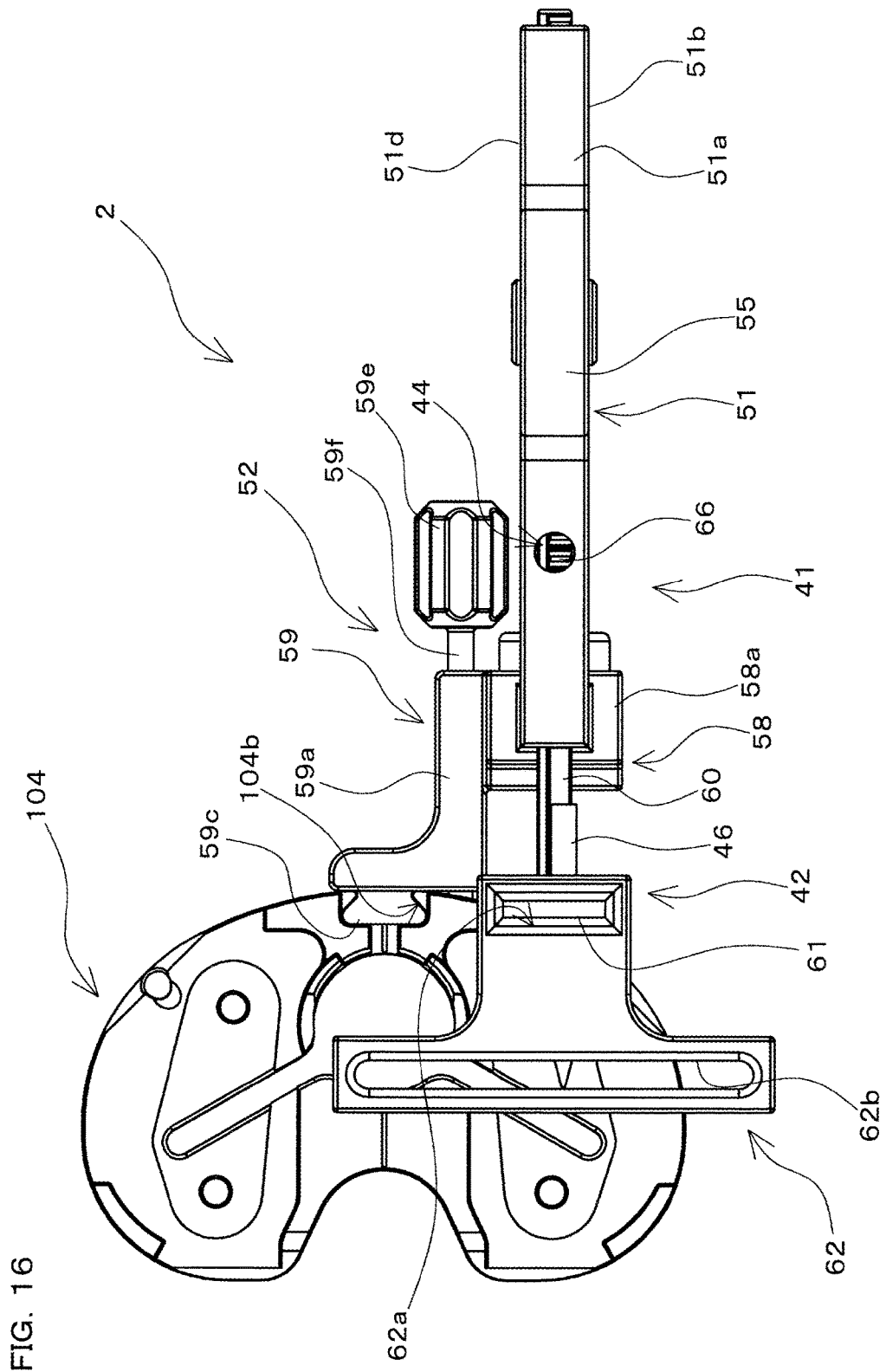
FIG. 16 is a plan view of the measurement instrument for joint surgery shown in FIG. 11 and a tibial tray trial.
Figure 17:
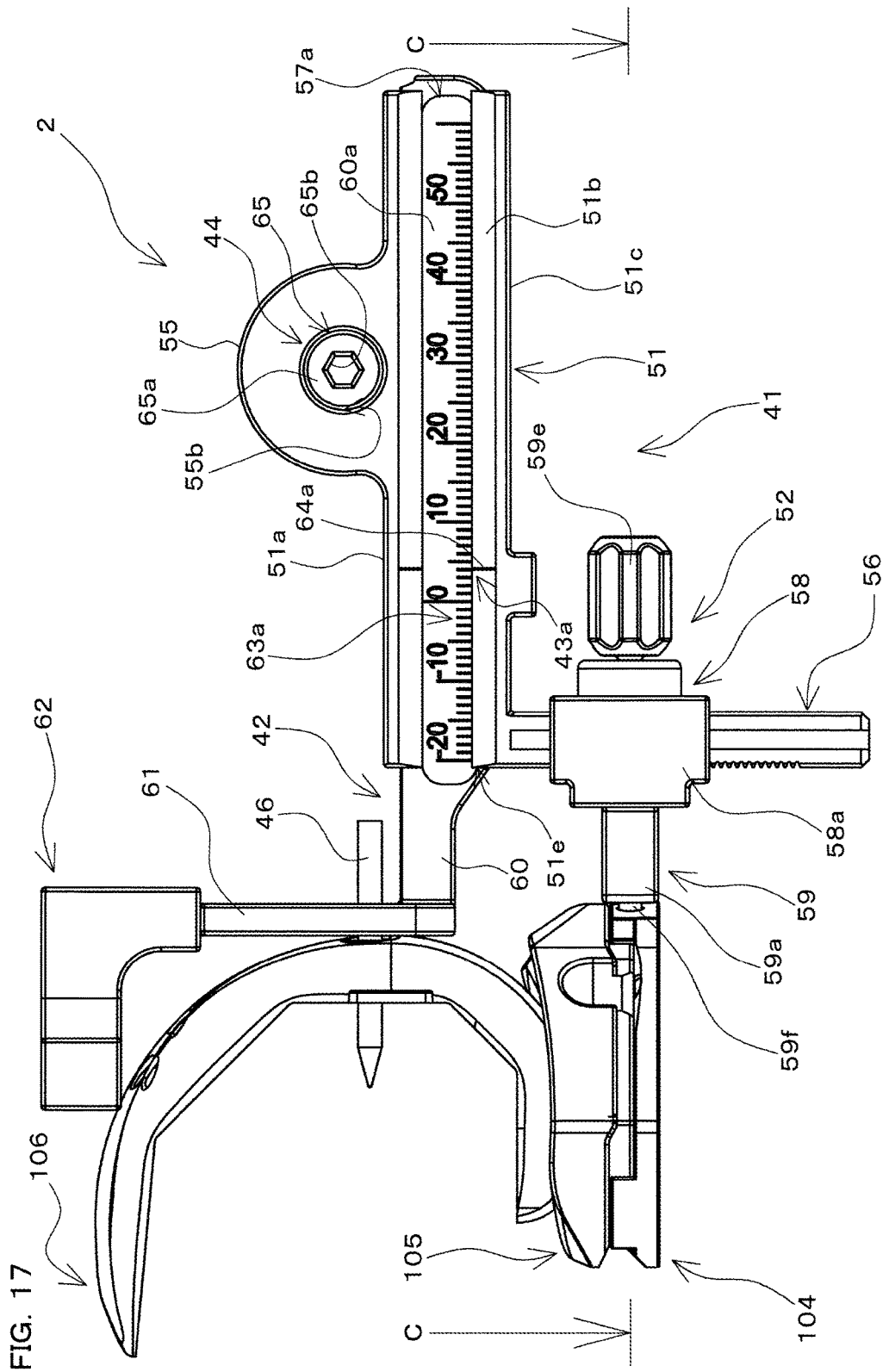
FIG. 17 is a side view of the measurement instrument for joint surgery shown in FIG. 11, the tibial tray trial, a tibial insertion trial, and a femur trial.
Figure 18:
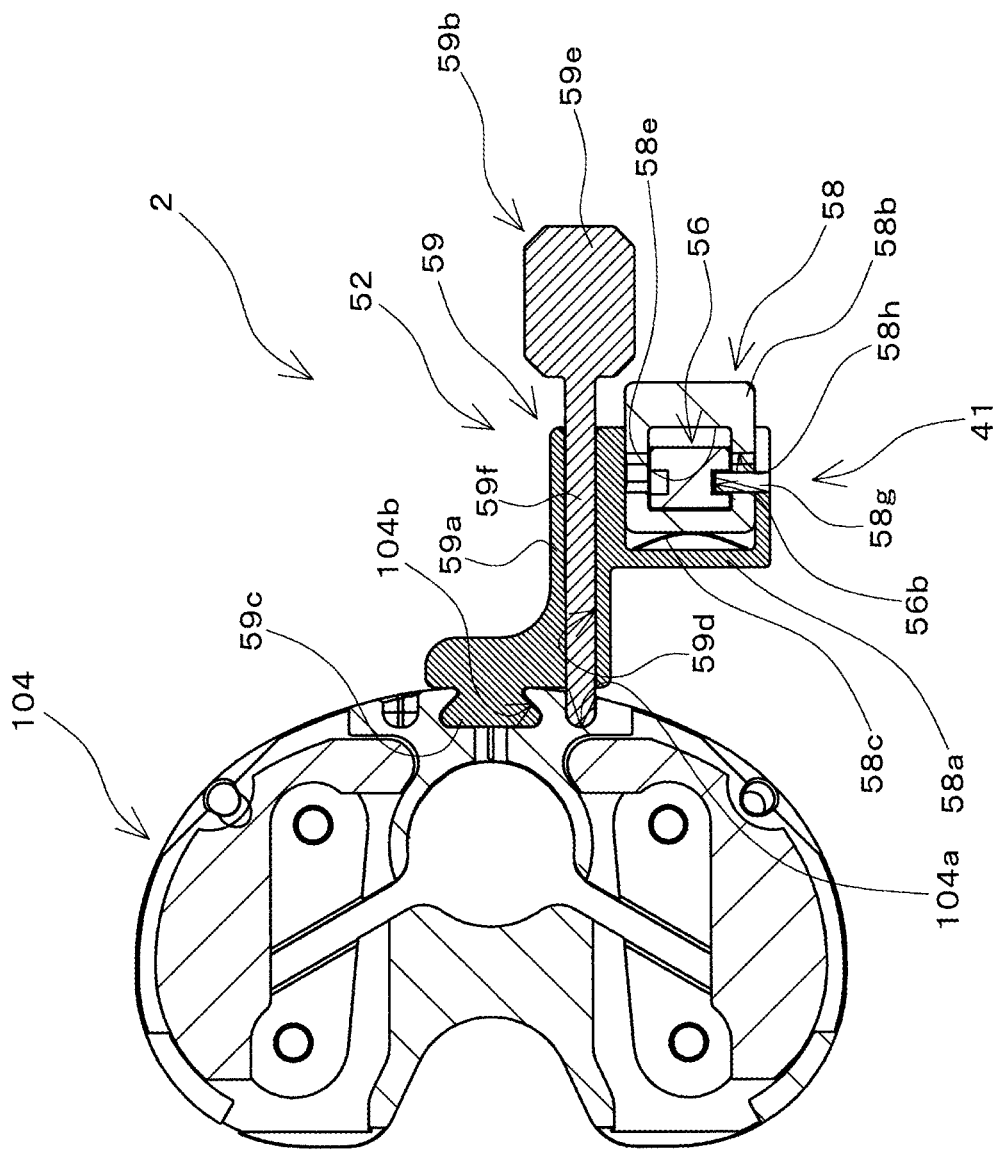
FIG. 18 is a cross-sectional view showing a cross section as viewed from the position of arrows C-C in FIG. 17.

Next, configurations of the measurement instrument for joint surgery 2 will be described. First, the housing 41 will be described. FIG. 14 is a plan view of the measurement instrument for joint surgery 2. FIG. 15 is a cross-sectional view showing a cross section as viewed from the position of arrows B-B in FIG. 14. FIG. 16 is a plan view of the measurement instrument for joint surgery 2 and the tibial tray trial 104. FIG. 17 is a side view of the measurement instrument for joint surgery 2, the tibial tray trial 104, the tibial insertion trial 105, and the femur trial 106. FIG. 18 is a cross-sectional view showing a cross section as viewed from the position of arrows C-C in FIG. 17.

The housing 41 shown in FIGS. 11 to 18 is provided so as to be able to be fixed to the tibia 101 or the tibial tray trial 104 that is a component attached to the tibia 101. Note that FIGS. 11 and 12 show the housing 41 that is fixed to the tibial tray trial 104. On the other hand, FIG. 13 shows the housing 41 that is fixed to the tibia 101.

The housing 41 is constituted by a housing body 51, a component fixing portion 52, a lid 53, a bone fixing block 54, and the like. The housing body 51 is provided as a body part of the housing 11, and is provided as a part that slidably supports the later-described slider 42. The housing body 51 is provided with a case-like part within which the later-described slider 42 is slidably arranged, a pinion arrangement portion 55 within which a pinion 65 in the later-described drive mechanism 44 is arranged, a connection support portion 56, and the like.

The aforementioned case-like part of the housing body 51 is constituted by four walls (51a, 51b, 51c, and 51d) that form a rectangular cross section. The wall 51a and the wall 51c are provided so as to extend parallel with each other, and the wall 51b and the wall 51d are provided parallel with each other. The wall 51b and the wall 51d are provided so as to extend in a direction perpendicular to the wall 51a and the wall 51c. Note that the wall 51b is divided into two smaller walls by an opening 57a, which extends to form a slit over the whole length of the case-like part of the housing body 51.

The wall 51a is provided with the pinion arrangement portion 55, the wall 51b is provided with the aforementioned slit-like opening 57a, and the wall 51d is provided with a window-like opening 57b. The openings (57a and 57b) are provided as openings that expose the entire or a part of gauges (63a and 63b) in the later-described position display portions (43a and 43b) to the outside of the housing body 51. The opening 57a is provided as a slit-like opening that extends in a direction in which the case-like part of the housing body 51 extends that is the longitudinal direction of the wall 51b. The opening 57h is provided as an elongated hole-like opening that extends in a direction in which the case-like part of the housing body 51 extends in a long manner that is the longitudinal direction of the wall 51d. For this reason, the openings (57a and 57b) are configured to be slits or elongated holes extending in a direction in which the slider 42 slides relative to the housing 41.

An opening 51e, which is open to the outside, is provided at one end of the housing body 51 in the longitudinal direction (see FIGS. 15 and 17). The later-described slider 42 is inserted into the housing 41 from the opening 51e of the housing body 51, and is arranged slidably.

The pinion arrangement portion 55 of the housing body 51 is provided as a part formed so as to rise cylindrically from the wall 51a to the outside. A space in which the pinion 65 in the later-described drive mechanism 44 is arranged is provided within the pinion arrangement portion 55.

The connection support portion 56 is provided as a columnar part that extends in a cantilevered manner from the case-like part of the housing body 51. The connection support portion 56 is provided so as to extend in a cantilevered manner in a direction perpendicular to the longitudinal direction of the case-like part of the housing body 51 at one end of the case-like part of the housing body 51. The later-described component fixing portion 52 is detachably attached and connected to the connection support portion 56, and the connection support portion 56 is provided as a part that supports the component fixing portion 52 relative to the housing body 51. Furthermore, the later-described bone fixing block 54 is also detachably attached and connected to the connection support portion 56, and the connection support portion 56 is also provided as a part that supports the bone fixing block 54 relative to the housing body 51.

The lid 53 is provided as a disk-like member in which a pinion support hole 53a, which is a through hole, is provided at the center (see FIGS. 11 and 13). The lid 53 is attached and fixed to the housing body 51. Note that the pinion arrangement portion 55 in the housing body 51 is provided with a circular hole 55a that is open on the wall 51d side (see FIGS. 11 and 13). The lid 53 is attached to the housing body 51 by being fitted into the hole 55a. Note that the outer-circumferential edge of the lid 53 and the inner-circumferential edge of the hole 55a may be fixed to each other by performing a joining process such as welding at a plurality of points, for example.

The pinion support hole 53a provided at the center of the lid 53 is provided as a hole that rotatably supports the later-described pinion 65. A pinion support hole 55b that rotatably supports the pinion 65 is also provided as a through hole on the wall 51b side in the pinion arrangement portion 55 (see FIGS. 12 and 17).

The component fixing portion 52 and the bone fixing block 54 are alternatively attached to the connection support portion 56. That is to say, when the component fixing portion 52 is attached to the connection support portion 56, the bone fixing block 54 is not attached to the connection support portion 56. When the bone fixing block 54 is attached to the connection support portion 56, the component fixing portion 52 is not attached to the connection support portion 56.

The component fixing portion 52 is detachably attached to the housing body 51 at the connection support portion 56, and is provided so as to be able to be fixed to the tibial tray trial 104 that is attached to the tibia 101. The component fixing portion 52 is provided with a connecting position adjustment portion 58 and a fixing operation portion 59.

The connecting position adjustment portion 58 is provided as a part of the component fixing portion 52 that is detachably attached to the housing body 51 at the connection support portion 56. The fixing operation portion 59 is provided as a part of the component fixing portion 52 that is fixed to the tibial tray trial 104 based on an operation made by the surgeon. A base 58a of the connecting position adjustment portion 58 and a base 59a of the fixing operation portion 59 are provided integrally.

The connecting position adjustment portion 58 is provided with the base 58a, a positioning member 58b, and a spring 58c. The base 58a is configured to be a rectangular tubular part, into which the connection support portion 56 is inserted. The base 58a is provided with an opening 58d, into which the positioning member 58b is inserted. The positioning member 58b is inserted into a space within the base 58a from the opening 58d in the base 58a. One end of the positioning member 58b inserted into the base 58a is arranged relative to the base 58a in a state of projecting from the base 58a (see FIGS. 11, 12, and 14 to 18).

The positioning member 58b is provided as a member for positioning the component fixing portion 52 relative to the housing body 51. More specifically, the positioning member 58b is provided as a member for positioning, in the longitudinal direction of the connection support portion 56, the component fixing portion 52 relative to the connection support portion 56.

The positioning member 58b is formed in a shape obtained by integrating a rectangular tubular part and a circular columnar part. The rectangular tubular part of the positioning member 58b is inserted into a space within the base 58a from the opening 58d in the base 58a. The circular columnar part of the positioning member 58b is arranged in a state of projecting from the base 58a, in a state where the rectangular tubular part of the positioning member 58b is inserted in the space within the base 58a (see FIGS. 11, 12, and 14 to 18). The circular columnar part of the positioning member 58b is provided as a part that is pressed by the surgeon when the surgeon relatively displaces and positions the component fixing portion 52 with respect to the connection support portion 56.

The connection support portion 56 is inserted into a through hole 58e having a square cross section within the rectangular tubular part of the positioning member 58b. The connection support portion 56 passes through the inside of the base 58a and also passes through the through hole 58e within the positioning member 58b in a loosely fitting manner. That is to say, the connection support portion 56 is arranged in a state of passing through the through hole 58e within the positioning member 58b that is inserted to the inside of the base 58a from the opening 58d (see FIGS. 15 and 18).

One of four inner-wall surfaces of the through hole 58e having a square cross section in the positioning member 58b is provided with recessed and projecting teeth 58f, which are formed by repeating small projecting parts and small groove-like parts (see FIG. 15). The recessed and projecting teeth 58f are provided in an inner-wall surface among the four inner-wall surfaces of the through hole 58e that is farthest from the circular columnar part of the positioning member 58b that projects to the outside from the base 58a. That is to say, the recessed and projecting teeth 58f are provided on the inner-wall surface among the four inner-wall surfaces of the through hole 58a that is arranged on the most distal side separately from the opening 58d in the base 58a.

The recessed and projecting teeth 58f of the positioning member 58b are provided so as to be able to mesh and engage with recessed and projecting teeth 56a, which are provided on an outer peripheral surface of the connection support portion 56 that passes through the through hole 58e in a loosely fitting manner. The recessed and projecting teeth 56a are provided on one surface on the outer periphery of the connection support portion 56, the one surface opposing the recessed and projecting teeth 58*f* of the positioning member 58*b*. Similar to the recessed and projecting teeth 58*f*, the recessed and projecting teeth 56*a* are formed by repetition of a small projecting part and a small groove-like part.

The spring 58*c* is arranged within the base 58*a*. The spring 58*c* is arranged on the most distal side from the opening 58*d* in the base 58*a*, and abuts against an inner-wall surface on the most distal side from opening 58*d* in the base 58*a*. In this embodiment, the spring 58*c* is provided as a flat spring that curves and rises at its center part. That is to say, the flat spring 58*c* is configured to act as a spring by undergoing elastic deformation such that the amount of the rising at the center part that curves and rises is small.

Within the base 58*a*, an end of the positioning member 58*b* on the side opposite to its circular columnar part abuts against the curving and rising part at the center of the spring 58*c*. That is to say, the end of the positioning member 58*b* that is arranged on the most distal side within the base 58*a* abuts against the spring 58*c*. The spring 58*c* biases the positioning member 58*b* toward the opening 58*d* side of the base 58*a* relative to the base 58*a* within the base 58*a*. That is to say, the spring 58*c* biases the positioning member 58*b* in a direction in which the positioning member 58*b* is projected to the outside from the inside of the base 58*a*.

A coming-off prevention pin 58*g*, which shortly projects to the inside in a cantilevered manner, is provided in one of the walls of the base 58*a* (see FIG. 18). The coming-off prevention pin 58*g* is fixed to one of the walls of the base 58*a* by welding, for example. The coming-off prevention pin 58*g* passes through a pin through hole 58*h*, which is formed to pass through the positioning member 58*a*, in a loosely fitting manner. Furthermore, a tip of the coming-off prevention pin 58*g* that passes through the pin through hole 58*h* is slidably fitted into a rail groove 56*b* provided in the connection support portion 56. The rail groove 56*b* is formed so as to extend in the connection support portion 56 in the longitudinal direction thereof. Due to the tip of the coming-off prevention pin 58*g* that passes through the pin through hole 58*h* fitting into the rail groove 56*b*, the positioning member 58*b* is prevented from coming off from the base 58*a* and falling off.

When attaching the connecting position adjustment portion 58 to the connection support portion 56, the surgeon initially presses the circular columnar part of the positioning member 58*b* that projects from the base 58*a* toward the base 58*a* side. Thus, the positioning member 58*a* is displaced to the distal side from the opening 58*d* in the base 58*a* against the biasing force of the spring 58*c*. At this time, the coming-off prevention pin 58*g* is also relatively displaced within the pin through hole 58*h*.

The connection support portion 56 is inserted into the base 58*a* in the above state. At this time, the connection support portion 56 is also inserted into the through hole 58*e* in the positioning member 58*h*. Furthermore, the tip of the coming-off prevention pin 58*g* is slidably fitted into the rail groove 56*b* in the connection support portion 56. In this state, the surgeon relatively displaces the connecting position adjustment portion 58 with respect to the connection support portion 56 up to a desired position in the longitudinal direction of the connection support portion 56. Note that the base 58*a* of the connecting position adjustment portion 58 and the base 59*a* of the fixing operation portion 59 are provided in an integrated manner, and the fixing operation portion 59 is relatively displaced together with the connecting position adjustment portion 58 with respect to the connection support portion 56. That is to say, the component fixing portion 52 is relatively displaced with respect to the connection support portion 56 in an integrated manner.

Then, upon the connecting position adjustment portion 58 reaching the desired position, the surgeon releases the pressing operation to the circular columnar part of the positioning member 58*b*. Thus, the positioning member 58*b* is biased to the opening 58*d* side from the inside of the base 58*a* by the biasing force of the spring 58*c*. The recessed and projecting teeth 58*f* of the positioning member 58*b* mesh with the recessed and projecting teeth 56*a* of the connecting position adjustment portion 56, and the recessed and projecting teeth 58*f* and the recessed and projecting teeth 56*a* engage with each other. Thus, the connecting position adjustment portion 58 is positioned relative to the connection support portion 56. That is to say, the component fixing portion 52 is positioned relative to the housing body 51.

Note that the above operation of positioning the connecting position adjustment portion 58 relative to the connection support portion 56 to a desired position is also performed as appropriate during knee joint surgery. Even after the connecting position adjustment portion 58 is attached to the connection support portion 56, the surgeon performs an operation similar to the above operation as necessary, and adjusts the position of the connecting position adjustment portion 58 relative to the connection support portion 56. For example, after the component fixing portion 52 is fixed to the fixing operation portion 59, an operation similar to the above operation is performed, and the position of the connecting position adjustment portion 58 relative to the connection support portion 56 is adjusted.

The fixing operation portion 59 is provided as a part that is to be fixed to the tibial tray trial 104 based on an operation made by the surgeon. Due to the fixing operation portion 59 being fixed to the tibial tray trial 104, the component fixing portion 52 including the fixing operation portion 59, and the housing body 51 to which the component fixing portion 52 is attached are fixed to the tibial tray trial 104. That is to say, the housing 41 is fixed to the tibial tray trial 104 by the fixing operation portion 59 being fixed to the tibial tray trial 104.

The fixing operation portion 59 is provided with the base 59*a*, a fixing shaft member 59*b*, and a projecting portion 59*c* (see FIGS. 11, 12, and 14 to 18). The base 59*a* is formed in an approximately L shape that extends to form a quadrangular prism and thereafter bends substantially at a right angle and extends. The base 59*a* is formed integrally with the base 58*a* of the connecting position adjustment portion 58.

The part of the base 59*a* that extends to form a quadrangular prism is provided so as to extend in a direction parallel with a direction in which the positioning member 58*h* is inserted in the base 58*a*. The part of the base 59*a* that extends to form a quadrangular prism is provided with a through hole 59*d* that a shaft 59*f* of the later-described fixing shaft member 59*b* is threaded with and passes through (see FIG. 18).

The fixing shaft member 59*b* is constituted by a handle 59*e* and the shaft 59*f*. The handle 59*e* is provided as a part that is held and to be subjected to a rotational operation by the surgeon when the fixing operation portion 59 is fixed to the tibial tray trial 104.

The shaft 59*f* is provided so as to be integrally combined with the handle 59*e*, and is provided as a threaded shaft part that extends linearly from the handle 59*e*. An external thread is formed on the outer circumference of the shaft 59*f*. The shaft 59*f* is arranged in a state of being threaded with and passing through the through hole 59*d* provided in the base

59a. Note that an internal thread that is to be threaded with the external thread on the shaft 59f is provided on the inner circumference of the through hole 59d. An end of the shaft 59f on the tip side is formed in a hemispherical shape. The end of the shaft 59f on the tip side is configured to be fitted into a fitting hole 104a that is provided in the tibial tray trial 104 (see FIG. 18).

The projecting portion 59c is provided integrally with the base 59a. The projecting portion 59c is provided as a part that projects from the part of the base 59a that bends substantially at a right angle and extends from the part extending to form a quadrangular prism. The projecting portion 59c projects so as to expand to the outside from the base 59a, and a flat end face is formed in a part at a leading end of the projecting portion 59c (see FIG. 18). Therefore, a region that is recessed at an acute angle is formed between the projecting portion 59c and the base 59a.

The projecting portion 59c is configured to be fitted into a recessed portion 104b that is provided in the tibial tray trial 104 (see FIG. 18). The recessed portion 104b is formed to be a groove-like part that is recessed so as to have an inner face corresponding to the exterior shape of the projecting portion 59c. A part of the recessed portion 104b demarcates a part that projects at an acute angle so as to be fitted into the region recessed at an acute angle formed between the projecting portion 59c and the base 59a. Therefore, the cross-sectional shape of the recessed portion 104b provided in a groove-like shape is formed such that, in a cross section in a direction substantially perpendicular to the bone axis direction of the tibia 101 onto which the tibial tray trial 104 is installed, the entrance side is narrow and the depth side expands.

When the fixing operation portion 59 is fixed to the tibial tray trial 104, initially, the projecting portion 59c is fitted into the recessed portion 104b in a direction substantially parallel with the bone axis direction of the tibia 101 onto which the tibial tray trial 104 is installed. At this time, the end of the shaft 59f of the fixing shaft member 59b on the tip side does not project from the base 59a and is located within the through hole 59d of the base 59a.

In the above state, the surgeon operates to rotate the handle 59e, and causes the fixing shaft member 59b to project from the base 59a. That is to say, the shaft 59f rotates together with the handle 59e, the threaded position of the external thread on the shaft 59f relative to the internal thread on the through hole 59d changes, and the end of the shaft 59f on the tip side projects from the base 59a. The end of the shaft 59f on the tip side that projects from the base 59a is fitted into the fitting hole 104a in the tibial tray trial 104. Upon the end of the shaft 59f on the tip side being fitted into the fitting hole 104a in the tibial tray trial 104, the surgeon stops the operation of rotating the handle 59e.

As mentioned above, after the projecting portion 59c is fitted into the recessed portion 104b and the end of the shaft 59f on the tip side enters a state of being fitted into the fitting hole 104a, the fixation of the fixing operation portion 59 to the tibial tray trial 104 is completed. Thus, the housing 41 is fixed to the tibial tray trial 104 by the fixing operation portion 59 being fixed to the tibial tray trial 104.

The bone fixing block 54 is attached to the connection support portion 56 when the measurement instrument for joint surgery 2 is used in a state where no component is attached to the tibia 101 and the femur 102, as shown in FIG. 13. The bone fixing block 54 is provided as a substantially rectangular parallelepiped member, attached to the connection support portion 56, and arranged between the connection support portion 56 and the tibia 101. The bone fixing block 54 is attached to the connection support portion 56 so as to keep the distance between the connection support portion 56 and the tibia 101 at a given distance. Due to the distance between the connection support portion 56 and the tibia 101 being kept at a given distance by the bone fixing block 54, the moving area of the slider 42 relative to the housing 41 can be sufficiently ensured.

The bone fixing block 54 is provided with a plurality of through holes into which the housing fixation pins 47 are inserted. Meanwhile, a plurality of pin insertion holes 56c are also formed so as to pass through the connection support portion 56 (see FIGS. 13 and 15). The plurality of through holes provided in the bone fixing block 54 and the plurality of pin insertion holes 56c in the connection support portion 56 are provided such that the position and the hole diameter of the through holes correspond to those of the pin insertion holes 56c.

When the bone fixing block 54 is attached to the connection support portion 56, the housing fixation pins 47 are inserted into both holes so as to pass through the pin insertion holes 56c in the connection support portion 56 and also pass through the through holes in the bone fixing block 54. The housing fixation pins 47 that have passed through the pin insertion holes 56c in the connection support portion 56 and the through holes in the bone fixing block 54 are driven into the tibia 101 to engage therewith. Thus, the connection support portion 56 and the bone fixing block 54 are fixed to the tibia 101 in a state where the bone fixing block 54 is attached to the connection support portion 56. That is to say, the housing 41 is fixed to the tibia 101.

Slider

The slider 42 shown in FIGS. 11 to 17 is provided so as to be able to slide relative to the housing 41. The slider 42 is provided so as to be able to abut against or be fixed to the femur 102 or the femur trial 106 that is a component attached to the femur 102. Note that FIGS. 11 and 12 show the slider 42 that is fixed to the femur trial 106. On the other hand, FIG. 13 shows the slider 42 that is fixed to the femur 102.

The slider 42 is constituted by a slider body 60, a paddle 61, and a femur-side fixing portion 62. The slider body 60 is provided as a body part of the slider 42, and is provided as a part that is supported so as to be able to slide relative to the housing body 51 of the housing 41. The slider body 60 is formed in a shape whose main part is an elongated rectangular parallelepiped part that extends linearly in a substantially rectangular cross section, for example. The slider body 60 is inserted into the housing body 51 of the housing 41 from the opening 51e in the longitudinal direction of the slider body 60. The slider body 60 is slidably arranged within the case-like part of the housing body 51 in the longitudinal direction of the housing body 51.

The slider body 60 is provided with three sliding faces (60a, 60b, and 60c) that extend in the longitudinal direction of the slider body 60 (see FIGS. 11 to 13, 15, and 17). The sliding face 60a and the sliding face 60c are configured to be faces extending parallel with each other. The sliding face 60b is configured to be a face perpendicular to the sliding face 60a and the sliding face 60c. The sliding face 60a, the sliding face 60b, and the sliding face 60c slide inward of the wall 51b, the wall 51c, and the wall 51d, respectively, with respect to the housing body 51.

The paddle 61 is provided integrally with the slider body 60, and is provided so as to extend in a cantilevered manner from one end of the slider body 60. Note that the one end of the slider body 60 is provided so as to project from the opening 51e at the end of the case-like part of the housing body 51. The paddle 61 is provided so as to extend from the one end of the slider body 60 to form an elongated flat-plate shape in a direction perpendicular to the longitudinal direction of the slider body 60. Note that the paddle 61 projects and extends from the slider body 60 so as to extend in a direction substantially parallel with the bone axis direction of the tibia 101 in a state where the measurement instrument for joint surgery 2 is installed on the knee joint.

A plurality of pin insertion holes 61a are formed in the paddle 61 so as to pass through the paddle 61 (see FIGS. 11, 13, and 15). The pin insertion holes 61a are provided as elongated holes that extend in a direction perpendicular to the longitudinal direction of the paddle 61. Therefore, in a state where the measurement instrument for joint surgery 2 is installed on the knee joint, the pin insertion holes 61a are elongated holes that extend in the left-right direction of the human body of a patient (see FIGS. 11 and 13).

A bending position holding pin 46, which passes through the femur trial 106 and is driven into the femur 102, is inserted into one of the pin insertion holes 61a in the paddle 61 in a loosely fitting state. That is to say, one end of the bending position holding pin 46 passes through the femur trial 106 and is driven into and engaged with the femur 102, and the other end is inserted into the pin insertion hole 61a.

Note that the bending position holding pin 46 is used for keeping the knee joint at a bending position and holding the relative position of the tibia 101 and the femur 102. In a state where the bending position holding pin 46 that is driven into the femur 102 is inserted in the pin insertion hole 61a as shown in FIG. 11, if the bending angle of the femur 102 relative to the tibia 101 is about to change, the movement of the bending position holding pin 46 is restricted by an edge part of the pin insertion hole 61a. Thus, the relative position of the tibia 101 and the femur 102 is held in a state where the knee joint is at the bending position.

The femur-side fixing portion 62 is provided as a part that is attached to the paddle 61 and fixed to the femur 102 or the femur trial 106 that is a component attached to the femur 102. A paddle fitting hole 62a having a rectangular cross section is provided in a part of the femur-side fixing portion 62 that is attached to the paddle 61. Due to an end of the paddle 61 on the side opposite to the slide body 42 side being fitted into the paddle fitting hole 62a, the femur-side fixing portion 62 is attached to the paddle 61.

An elongated pin insertion hole 62b is provided in a part of the femur-side fixing portion 62 that is attached to the femur 102 or the femur trial 106. The femur-side fixing portion 62 is fixed to the femur 102 or the femur trial 106 via slider fixation pins 45 that are inserted into the pin insertion hole 62b. Note that the pin insertion hole 62b is provided as an elongated hole that extends in the left-right direction of the human body of the patient in a state where the measurement instrument for joint surgery 2 is installed on the knee joint, as shown in FIGS. 11 and 13.

Note that, in the mode shown in FIGS. 11 and 12, the slider fixation pins 45 that pass through the pin insertion hole 62b are inserted into through holes 106b provided in the femur trial 106, and are further driven into and engaged with the femur 102. Therefore, the femur-side fixing portion 62 is fixed to the femur trial 106 and the femur 102 via the slider fixation pins 45. Thus, the slider 42 is fixed to the femur trial 106 and the femur 102.

On the other hand, in the mode shown in FIG. 13, the slider fixation pins 45 that pass through the pin insertion hole 62b are driven into and engaged with the femur 102. Therefore, the femur-side fixing portion 62 is fixed to the femur 102 via the slider fixation pins 45. Thus, the slider 42 is fixed to the femur 102.

Note that, although FIGS. 11 to 13 show the mode in which a plurality of slider fixation pins 45 that are inserted in the pin insertion hole 62b are fixed to the femur trial 106 or the femur 102, this need not be the case. A mode may be implemented in which one slider fixation pin 45 inserted in the pin insertion hole 62b is fixed to the femur trial 106 or the femur 102. In the case of being fixed by the plurality of slider fixation pins 45, pivoting movement of the femur 102 relative to the tibia 101 around the bone axis of the tibia 101 is restricted. On the other hand, in the case of being fixed by one slider fixation pin 45, pivoting movement of the femur 102 relative to the tibia 101 around the bone axis of the tibia 101 is likely to be allowed. The number of slider fixation pins 45 to be used for the fixation may be selected as appropriate by the surgeon according to the necessity during joint surgery.

Position Display Portion

The position display portions (43a and 43b) shown in FIGS. 11 to 13 and 17 are provided as a mechanism that displays the position of the slider 42 relative to the housing 41. The position display portion 43a is provided in the wall 51b of the housing body 51 of the housing 41 and the sliding face 60a of the slider body 60 of the slider 42. The position display portion 43b is provided in the wall 51d of the housing body 51 of the housing 41 and the sliding face 60c of the slider body 60 of the slider 42. The position display portion 43a and the position display portion 43b are configured in a similar manner.

The position display portion 43a is constituted by a gauge 63a and a reading position indicating portion 64a. The gauge 63a is provided in one of the housing 41 and the slider 42. In this embodiment, the gauge 63a is provided in the slider 42. More specifically, the gauge 63a is configured to be a gauge that is marked at even intervals in the sliding face 60a of the slider body 60 of the slider 42. For example, the gauge 63a is configured to be a plurality of groove-like marks marked at intervals of 1 millimeter in the sliding face 60a. Note that, in the sliding face 60a, values corresponding to some of the marks are marked together with the plurality of marks in the gauge 63a.

The reading position indicating portion 64a is provided in the other one of the housing 41 and the slider 42. In this embodiment, the reading position indicating portion 64a is provided in the housing 41. The reading position indicating portion 64a is provided as a mark indicating a reading position in the gauge 63a. More specifically, the reading position indicating portion 64a is configured to be a groove-like mark marked near the opening 57a in the wall 51b of the housing body 51.

When the slider 42 slides relative to the housing 41 in the longitudinal direction of the housing body 51 of the housing 41, the gauge 63a is always exposed from the opening 57a. Upon the slider 42 sliding relative to the housing 41, the plurality of marks in the gauge 63a are relatively displaced with respect to the opening 57a and the reading position indicating portion 64a. Therefore, when the slider 42 slides relative to the housing 41, the amount of relative movement of the slider 42 with respect to the housing 41 is ascertained by ascertaining the position of the gauge 63a that corresponds to the position of the reading position indicating portion 64a before and after the sliding.

The position display portion 43b is constituted by a gauge 63b and a reading position indicating portion 64b. The gauge 63b is provided in the slider 42, and is configured to be a gauge marked at equal intervals in the sliding face 60c of the slider body 60 of the slider 42. For example, the gauge 63b is configured to be a plurality of groove-like marks marked at intervals of 1 millimeter in the sliding face 60c.

The reading position indicating portion 64b is provided in the housing 41, and is provided as a mark indicating a reading position in the gauge 63b. More specifically, the reading position indicating portion 64b is configured to be a groove-like mark marked near the opening 57b in the wall 51d of the housing body 51.

When the slider 42 slides relative to the housing 41 in the longitudinal direction of the housing body 51 of the housing 41, a part of the gauge 63b is always exposed from the opening 57b. Upon the slider 42 sliding relative to the housing 41, the plurality of marks in the gauge 63b are relatively displaced with respect to the opening 57b and the reading position indicating portion 64b. Therefore, when the slider 42 slides relative to the housing 41, the amount of relative movement of the slider 42 with respect to the housing 41 is ascertained by ascertaining the position of the gauge 63b that corresponds to the position of the reading position indicating portion 64b before and after the sliding.

Drive Mechanism

The drive mechanism 44 shown in FIGS. 11 to 17 is provided as a mechanism that drives the slider 42 so as to slide relative to the housing 41. In this embodiment, the drive mechanism 44 is provided as a rack-and-pinion mechanism, and is constituted by the pinion 65 and a rack 66. The pinion 65 is constituted by a gear that is provided on its outer circumference, and is provided as a driving force input portion to which a driving force in a rotational direction from the outside is input. The pinion 65 is provided with a shaft 65a at its center part, and the gear is provided on the outer circumference of the center part of the shaft 65a in its axial direction.

The pinion 65 is attached to the housing 41. The pinion 65 is arranged within the pinion arrangement portion 55 of the housing body 51, and is rotatably supported relative to the housing 41. The pinion 65 is rotatably supported relative to the housing 41 at both ends of the shaft 65a. Specifically, one end of the shaft 65a is inserted into the pinion support hole 55b provided in the pinion arrangement portion 55, and the one end of the shaft 65a is rotatably supported relative to the pinion arrangement portion 55. The other end of the shaft 65a is inserted into the pinion support hole 53a provided in the lid 53, and the other end of the shaft 65a is rotatably supported relative to the lid 53. With the above configuration, the pinion 65 is rotatably supported relative to the housing 41.

Note that, when the pinion 65 is attached to the housing 41, initially, the pinion 65 is arranged within the pinion arrangement portion 55 with the one end of the shaft 65a inserted in the pinion support hole 55b. Then, the lid 53 is attached and fixed to the housing body 51 such that the other end of the shaft 65a is inserted in the pinion support hole 53a.

Figure 19:
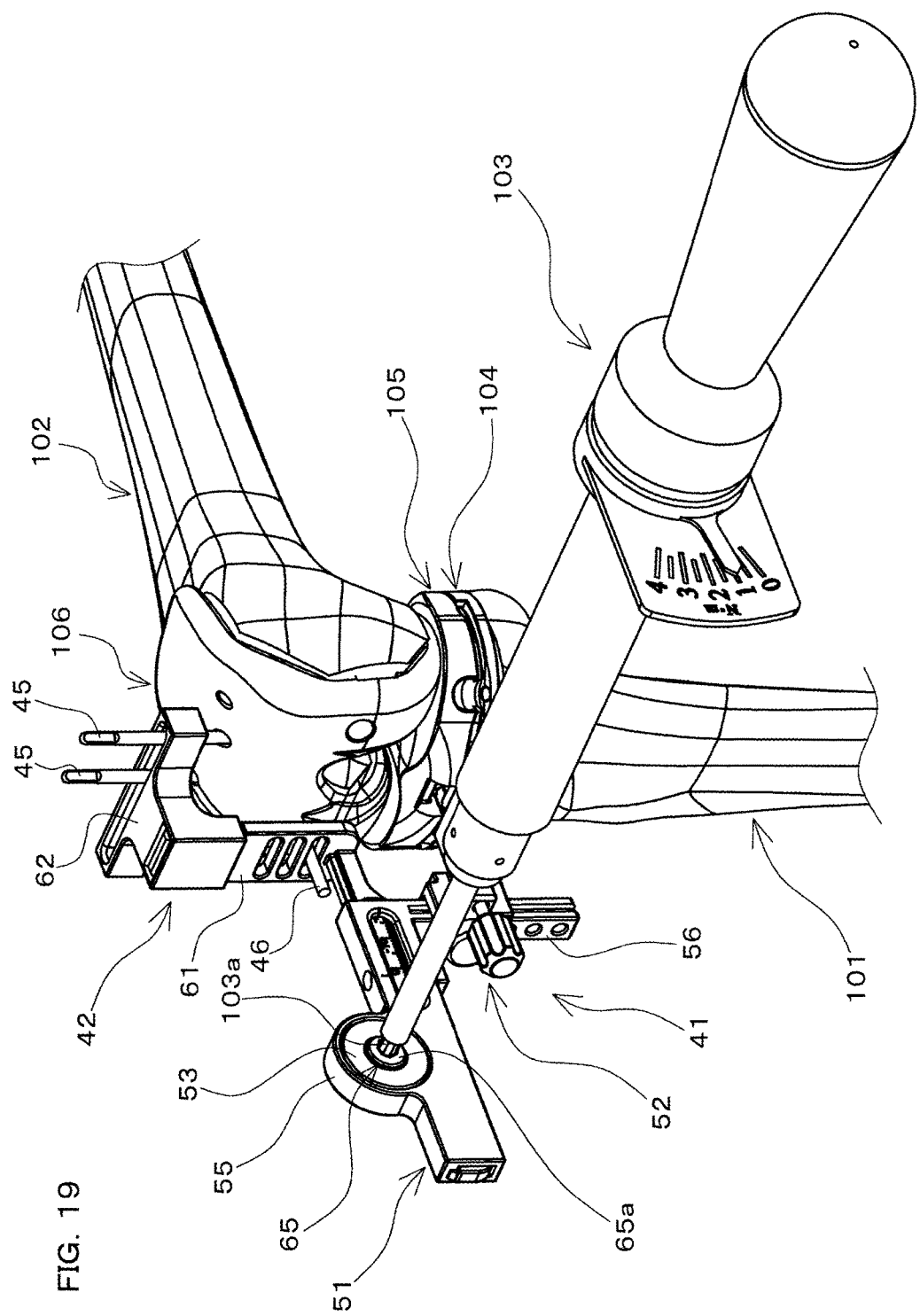
FIG. 19 is a schematic view showing a form of use of the measurement instrument for joint surgery shown in FIG. 11.

FIG. 19 is a schematic view showing a form of use of the measurement instrument for joint surgery 2. FIG. 19 shows the torque driver 103, which is an example of a device that is used together with the measurement instrument for joint surgery 2. The torque driver 103 is used as a torque generation device that generates a driving force in a rotational direction to be input to the drive mechanism 44.

A connection hole 65b, which is to be connected to the toque input shaft 103a at the tip of the torque driver 103, is provided in the shaft 65a of the pinion 65 (see FIGS. 11 to 13, 15, 17, and 19). The connection hole 65b is provided as a hole having a polygonal cross section that passes through the shaft 65a in the axial direction. The cross section of the torque input shaft 103a is also formed to be a polygonal cross section. The inner-circumferential cross section of the connection hole 65b is formed into a shape corresponding to the cross-sectional shape of the torque input shaft 103a.

When operating the drive mechanism 44 with the driving force of the torque driver 103, initially, the torque input shaft 103a at the tip of the torque driver 103 is inserted into the connection hole 65b. Thus, the torque input shaft 103a is fitted into the connection hole 65b, and the connection hole 65b in the pinion 65 and the torque input shaft 103a of the torque driver 103 are connected. As a result of the torque driver 103 being operated with the torque input shaft 103a of the torque driver 103 inserted, a rotational driving force from the torque driver 103 is input to the pinion 65 connected to the torque input shaft 103a.

The rack 66 shown in FIGS. 14 to 16 is provided in the slider body 60 of the slider 42, and is provided as linearly arrayed teeth that mesh with the gear of the pinion 65. The rack 66 is provided as a sliding drive portion that converts the driving force in the rotational direction that is input from the torque driver 103 to the pinion 65 into a driving force in a linear direction, and slides the slider 42 relative to the housing 41.

The rack 66 is arranged so as to oppose the wall 51a in a state where the slider body 60 is arranged within the housing body 51. A part of an inner circumferential wall that demarcates the space within the pinion arrangement portion 55 of the housing body 51 is open to a space where the slider 42 is arranged inside the case-like part of the housing body 51. The gear of the pinion 65 and the linear teeth of the rack 66 mesh with each other via the aforementioned opening provided in the inner-circumferential wall of the pinion arrangement portion 55.

Upon the rotational driving force from the torque driver 103 being input to the pinion 65, the pinion 65 that is rotationally supported by the housing 41 rotates. With the rotation of the pinion 65, the rack 66 that meshes with the pinion 65 moves together with the slider 42 in the longitudinal direction of the housing body 51 of the housing 41. Thus, the slider 42 slides relative to the housing 41 in the longitudinal direction of the housing body 51 of the housing 41. The drive mechanism 44 is configured to be able to, by the rotational driving force from the torque driver 103 being input thereto, slide the slider 42 relative to the housing 41 between a more withdrawn state and a more projecting state in accordance with the rotational direction of the pinion 65.

Operation of Measurement Instrument for Joint Surgery

Next, the operation of the measurement instrument for joint surgery 2 will be described. The measurement instrument for joint surgery 2 is used in knee joint surgery. In the knee joint surgery, initially, an incision is made in a part of the skin near the knee joint, and a part of the knee joint is exposed to the outside.

In the case of the form of use shown in FIGS. 11 and 12, an excision face 101b is formed at an end of the tibia 101 on the proximal side, and an excision face 102b is formed at an end of the femur 102 on the distal side. After the excision faces (101b and 102b) have been formed, the tibial tray trial 104 and the tibial insertion trial 105 are installed at the end of the tibia 101 on the proximal side, and the femur trial 106 is installed at the end of the femur 102 on the distal side. The measurement instrument for joint surgery 2 is used in this state as shown in FIGS. 11 and 12.

On the other hand, in the case of the form of use shown in FIG. 13, the measurement instrument for joint surgery 2 is used in a state where the end of the tibia 101 on the proximal side and the end of the femur 102 on the distal side have not been excised. As shown in FIG. 13, the measurement instrument for joint surgery 2 is used in a state where the tibial tray trial 104, the tibial insertion trial 105, and the femur trial 106 are not installed on the tibia 101 and the femur 102.

Note that the following description of the operation of the measurement instrument for joint surgery 2 will be given mainly in terms of the form of use shown in FIGS. 11 and 12.

The measurement instrument for joint surgery 2 in which the component fixing portion 52 is attached to the housing body 51 is used in a state where the aforementioned trials (104, 105, and 106) are installed on the tibia 101 and the femur 102. When the measurement instrument for joint surgery 2 is used, initially, the fixing operation portion 59 of the component fixing portion 52 is fixed to the tibial tray trial 104.

When the fixing operation portion 59 is fixed to the tibial tray trial 104, as mentioned above, the projecting portion 59c of the fixing operation portion 59 is fitted into the recessed portion 104b of the tibial tray trial 104. The handle 59e is operated to rotate with the projecting portion 59c fitted into the recessed portion 104b, and the shaft 59f of the fixing shaft member 59b projects from the base 59a. Then, as mentioned above, the end of the shaft 59f on the tip side that projects from the base 59a is fitted into the fitting hole 104a in the tibial tray trial 104. Thus, the operation of fixing the component fixing portion 52 to the tibial tray trial 104 is completed.

After the component fixing portion 52 is fixed to the tibial tray trial 104, next, the connecting position adjustment portion 58 is operated as mentioned above, and the relative position of the housing body 51 with respect to the component fixing portion 52 is adjusted. More specifically, the circular columnar part of the positioning member 58b is pressed, and the meshing between the recessed and projecting teeth 58f and the recessed and projecting teeth 56a is released against the biasing force of the spring 58c. Thus, the engagement between the recessed and projecting teeth 58f and the recessed and projecting teeth 56a is released. In this state, the position of the connection support portion 56 relative to the connecting position adjustment portion 58 is changed so as to be relatively displaced up to the position desired by the surgeon. Upon the connection support portion 56 being relatively displaced up to the position desired by the surgeon, the pressing of the circular columnar part of the positioning member 58b is released. Thus, the recessed and projecting teeth 58f and the recessed and projecting teeth 56a are meshed and engaged with each other by the biasing force of the spring 58c, and the connection support portion 56 is positioned relative to the connecting position adjustment portion 58. That is to say, the housing body 51 is positioned relative to the component fixing portion 52.

Upon the positioning of the housing body 51 relative to the component fixing portion 52 being completed, the surgeon slides the slider 42 relative to the housing 41 in a direction projecting from the housing 41. The surgeon slides the slider 42 relative to the housing 41 up to a position where the paddle 61 lightly comes into contact with the joint face 106a of the femur trial 106. Upon the paddle 61 lightly coming into contact with the joint face 106a, the surgeon stops sliding the slider 42 relative to the housing 41.

Note that, before the component fixing portion 52 is fixed to the tibial tray trial 104, an operation in which the bending position holding pin 46 passes through the femur trial 106 and is driven into the femur 102 is performed. In a state where the surgeon has stopped sliding the slider 42 relative to the housing 41 as mentioned above, an end of the bending position holding pin 46 that projects from the femur trial 106 is inserted in a loosely fitted state into one of the pin insertion holes 61a in the paddle 61.

After having moved the slider 42 up to the position where the paddle 61 comes into contact with the femur trial 106 as mentioned above, the surgeon then inserts the slider fixation pins 45 into the pin insertion hole 62a in the femur-side fixing portion 62. The surgeon then inserts the slider fixation pins 45 into the through holes 106b in the femur trial 106, and further drives the slider fixation pins 45 into the femur 102 to engage the slider fixation pins 45 therewith. Thus, the slider 42 is fixed to the femur trial 106 and the femur 102.

The position of the slider 42 relative to the housing 41 is read in a state where the paddle 61 is lightly in contact with the joint face 106a of the femur trial 106 and the slider 42 is fixed to the femur trial 106 and the femur 102, as mentioned above. That is to say, the position of the slider 42 relative to the housing 41 is read by the surgeon using the position display portion 43a or the position display portion 43b. More specifically, the position of the mark indicated in the gauge 63a or the gauge 63b by the reading position indicating portion 64a or the reading position indicating portion 64b is read.

After the position of the slider 42 relative to the housing 41 has been read in the above state, next, the torque input shaft 103a of the torque driver 103 is connected to the connection hole 65b in the pinion 65 (see FIG. 19). Then, the surgeon operates the torque driver 103 to input the rotational driving force to the pinion 65 and operate the drive mechanism 44, and slides the slider 42 relative to the housing 41.

When the torque driver 103 is operated as mentioned above, the component fixing portion 52 of the housing 41 is fixed to the tibial tray trial 104, and the femur-side fixing portion 62 of the slider 42 is fixed to the femur trial 106. Then, the housing 41 and the slider 42 are arranged in a state where the longitudinal direction of the case-like part of the housing body 51 and the slider body 60 extend in the anterior-posterior direction of the patient.

As a result of the above, after the torque driver 103 is operated and the drive mechanism 44 operates, the drive mechanism 44 drives the slider 42 so as to slide relative to the housing 41 in the anterior-posterior direction of the patient. At this time, the surgeon inputs the rotational driving force from the torque driver 103 to the pinion 65 so as to slide the slider 42 relative to the housing 41 in a direction from the posterior face side to the anterior face side of the patient, for example. Thus, the measurement instrument for joint surgery 2 is configured to relatively move the femur 102, which is the second bone, relative to the tibia 101, which is the first bone, in the anterior-posterior direction along the joint faces (105a and 106a) between the tibia 101 and the femur 102, as a result of the slider 42 sliding relative to the housing 41. Note that, as mentioned above, the joint face 105a is a joint face of the tibial insertion trial 105 installed at the end of the tibia 101 on the proximal side, and the joint face 106a is a joint face of the femur trial 106 installed at end of the femur 102 on the distal side.

With the measurement instrument for joint surgery 2, the surgeon relatively moves the end of the femur 102 relative to the end of the tibia 101 along the joint faces in the anterior-posterior direction, and checks the stability of the state of connection between the tibia 101 and the femur 102 that are connected by soft tissue such as ligaments, as described above. Then, the surgeon stops operating the torque driver 103 after having moved the femur 102 relative to the tibia 101 to the extent required for checking the stability of the state of connection between the tibia 101 and the femur 102. More specifically, the surgeon stops operating the torque driver 103 at the point when a desired torque of a given magnitude is exerted.

After stopping operation the torque driver 103, the surgeon reads the position of the slider 42 relative to the housing 41 using the position display portion 43a or the position display portion 43b. More specifically, the surgeon reads the position of the mark indicated in the gauge 63a or the gauge 63b by the reading position indicating portion 64a or the reading position indicating portion 64b.

As described above, when the stability of the state of connection between the tibia 101 and the femur 102 is checked, initially, the position of the slider 42 relative to the housing 41 in a state where the paddle 61 of the slider 42 is lightly in contact with the femur trial 106 is read. Next, the surgeon operates the torque driver 103 until a desired torque of a given magnitude is exerted, slides the slider 42 relative to the housing 41, and moves the femur 102 relative to the tibia 101. The position of the slider 42 relative to the housing 41 is read in this state. Then, the amount of relative movement when the femur 102 relatively moves with respect to the tibia 101 along the joint faces (105a and 106a) is measured as a difference between the first-read position of the slider 42 relative to the housing 41 and the latter-read position of the slider 42 relative to the housing 41. Thus, with the measurement instrument for joint surgery 2, the stability of the state of connection between the tibia 101 and the femur 102 is measured based on the position of the slider 42 relative to the housing 41 displayed by the position display portion 43a or the position display portion 43b.

Note that in the case of the form of use shown in FIG. 13, the bone fixing block 54, rather than the component fixing portion 52, is attached to the housing body 51. The housing body 51 and the bone fixing block 54 are fixed to the tibia 101 via the housing fixation pins 47. Meanwhile, the slider 41 is fixed to the femur 102 via the slider fixation pins 45 in a state where the paddle 61 is lightly in contact with the anterior face side of the end of the femur 102. Then, an operation similar to that in the case of the above-described form of use (the form of use shown in FIGS. 11 and 12) is performed, and the stability of the state of connection between the tibia 101 and the femur 102 is measured based on the position of the slider 42 relative to the housing 41 displayed by the position display portion 43a or the position display portion 43b.

Effects of Measurement Instrument for Joint Surgery

As described above, according to this embodiment, the housing 41 is fixed to the tibia 101 or the tibial tray trial 104 that is attached to the tibia 101. Meanwhile, the slider 42 is fixed to the femur 102 or the femur trial 106 that is attached to the femur 102. In this state, the measurement instrument for joint surgery 2 is operated such that the slider 42 slides relative to the housing 41. Thus, the femur 102 is relatively moved with respect to the tibia 101 along the joint faces (105a and 106a) or the joint faces (101a and 102a). Then, the amount of relative movement when the femur 102 relatively moves with respect to the tibia 101 along the joint faces (105a and 106a) or the joint faces (101a and 102a) is measured based on the position of the slider 42 relative to the housing 41 displayed by the position display portions (43a and 43b). Thus, with this measurement instrument for joint surgery 2, the tibia 101 and the femur 102 that are connected by soft tissue at a joint are relatively moved along the joint faces (105a and 106a) or the joint faces (101a and 102a) between these bones, and the stability of the state of connection between these bones is measured as the amount of relative movement in the directions along the joint faces (105a and 106a) or the joint faces (101a and 102a). That is to say, with this measurement instrument for joint surgery 2, the stability of the state of connection between the tibia 101 and the femur 102 can be measured by relatively moving these bones in directions other than directions in which the tibia 101 and the femur 102 are separated from each other.

As described above, this embodiment can provide the measurement instrument for joint surgery 2 that can relatively move the tibia 101 and the femur 102 that are connected by soft tissue at a joint, in directions other than directions in which these bones are separated from each other, and measure the stability of the state of connection between these bones.

In addition, according to this embodiment, the stability of the state of connection between the tibia 101 and the femur 102 can be measured using the measurement instrument for joint surgery 2 in both states where the components (the tibial tray trial 104 and the tibial insertion trial 105) are attached to the tibia 101 and are not attached thereto. That is to say, in a state where the components are attached to the tibia 101, the measurement instrument for joint surgery 2 can be used by attaching the component fixing portion 52 to the housing body 51. On the other hand, in a state where the components are not attached to the tibia 101, the measurement instrument for joint surgery 2 can be used by removing the component fixing portion 52 from the housing body 51 and attaching the bone fixing block 54 to the housing body 51.

Modification

Although the embodiments of the present invention have been described above, the present invention is not limited to the above embodiments, and various modifications are possible within the scope recited in the claims. For example, the following modifications may be implemented.

(1) The above first and second embodiments have been described, taking, as an example, the mode in which the measurement instrument for joint surgery is used in knee joint surgery. However, this need not be the case. A measurement instrument for joint surgery that is used in elbow joint surgery or foot joint surgery may be implemented.

(2) The above first embodiment has been described, taking, as an example, the mode of the housing that can be fixed to the first bone. However, this need not be the case. As described as an example in the second embodiment, the mode of a housing that can be fixed to a component attached to the first bone may be implemented. As a modification of the first embodiment, a mode in which the first bone contact portion is fixed to the aforementioned component may be implemented.

(3) The above first embodiment has been described, taking, as an example, the mode of the slider that can abut against the second bone. However, this need not be the case. As described as an example in the second embodiment, a mode of a slider that can be fixed to the second bone may be implemented. As a modification of the first embodiment, a mode in which the second bone contact portion is fixed to the second bone may be implemented. Also, as a modification of the first embodiment, a mode of a slider that can abut against or fixed to a component attached to the second bone may be implemented. In this case, a mode in which the second bone contact portion abuts against or is fixed to the aforementioned component may also be implemented.

(4) The above first and second embodiments have been described, taking, as an example, the mode of the position display portion in which the gauge is provided in the slider and the reading position indicating portion is provided in the housing. However, this need not be the case. A mode of the position display portion in which the gauge is provided in the housing and the reading position indicating portion is provided in the slider may be employed.

(5) The above first and second embodiments have been described, taking, as an example, the mode in which a tensile force generated by soft tissue that connects the first bone and the second bone is measured by the torque driver. However, this need not be the case. A mode in which a tensile force generated by soft tissue that connects the first bone and the second bone is measured by a spring or a load cell that is included in the measurement instrument for joint surgery may be implemented.

(6) The above first embodiment has been described, taking, as an example, a mode in which the first curved portion is provided in the housing and the second curved portion is provided in the slider. However, this need not be the case. A measurement instrument for joint surgery in which not the first curved portion but a first chamfered portion is provided in the housing, and not the second curved portion but a second chamfered portion is provided in the slider may be implemented. That is to say, a mode may be implemented in which, in the housing, the first chamfered portion is provided on a corner at the end of the body part of the housing at which the first bone contact portion projects, the corner being on the side opposite to the side where the first bone contact portion projects, and in the slider, the second chamfered portion is provided on a corner at the end of the body part of the slider at which the second bone contact portion projects, the corner being on the side opposite to the side where the second bone contact portion projects.

According to the above modification, since the first chamfered portion is provided in the housing, it is possible to prevent the second bone and the corner of the housing on the side opposite to the side where the first bone contact portion projects from coming into contact and interfering with each other. In addition, since the second chamfered portion is provided in the slider, it is possible to prevent the first bone and the corner of the slider on the side opposite to the side where the second bone contact portion projects from coming into contact and interfering with each other. Accordingly, when the second bone is relatively moved with respect to the first bone along the joint faces by the measurement instrument for joint surgery, or when the angle of a joint constituted by an end of the first bone and an end of the second bone is changed with the measurement instrument for joint surgery arranged near the joint, it is possible to prevent the occurrence of interference between the first and second bones and the measurement instrument for joint surgery due to contact that is not intended by the surgeon.

(7) The above second embodiment has been described, taking, as an example, the mode in which the bone fixing block is attached to the housing body from which the component fixing portion has been removed, and the housing is fixed to the first bone. However, this need not be the case. A mode in which the bone fixing block is not provided, and the housing body is directly fixed to the first bone may be implemented. In this case, the shape of the housing body may be changed in order to keep a wider movable area of the slider relative to the housing. More specifically, the shape of the housing body may be changed so as to eliminate a part of the end of the housing body such that the movement of the slide is not readily restricted by the shape of the end of the housing body.

INDUSTRIAL APPLICABILITY

The present invention can be widely applied as a measurement instrument for joint surgery that is used in joint surgery.

DESCRIPTIONS OF REFERENCE NUMERALS

1 Measurement instrument for joint surgery
11 Housing
12 Slider
13a, 13b Position display portion
101 Tibia (first bone)
102 Femur (second bone)
101a, 102a Joint face

The invention claimed is:

1. A measurement instrument used in joint surgery to measure stability of a state of connection between a first bone and a second bone that are connected by soft tissue at a joint, comprising:
    a housing comprising a first part configured to be fixed to a component attached to the first bone;
    a slider configured to slide with respect to the housing in a first direction, and comprising a second part which is configured to abut against or be fixed to the second bone or a component attached to the second bone and is located next to the first part in a second direction intersecting the first direction; and
    a position display portion that displays a position of the slider relative to the housing,
    wherein the housing includes:
    a housing body that slidably supports the slider; and
    a component fixing portion that is detachably attached to the housing body and is configured to be fixed to the component attached to the first bone,
    wherein the second bone is configured for relative movement with respect to the first bone along a joint face that is between the first bone and the second bone by the slider sliding relative to the housing, and
    the stability of the state of connection between the first bone and the second bone is configured to be measured based on the position of the slider relative to the housing, wherein the position is displayed by the position display portion.

2. The measurement instrument for joint surgery according to claim 1,
    wherein the housing is provided with a first bone contact portion that projects in a cantilevered manner from a body part of the housing, the first bone contact portion configured to contact and be fixed to the first bone or the component attached to the first bone,
    wherein the slider is provided with a second bone contact portion that projects in a cantilevered manner from a body part of the slider, the second bone contact portion configured to contact against or be fixed to the second bone or the component attached to the second bone, and
    wherein the first bone contact portion and the second bone contact portion extend in a cantilevered manner in opposite directions that are parallel with the second direction intersecting the first direction of the slider relative to the housing.

3. The measurement instrument for joint surgery according to claim 2,
    wherein the housing is provided with a first chamfered portion or a first curved portion having a curved surface that curves, on a corner at an end of the body part of the housing, at which the first bone contact portion projects, and the corner being on a side of the housing from which the first bone contact portion projects, and wherein the slider is provided with a second chamfered portion or a second curved portion having a curved surface that curves, on a corner at an end of the body part of the slider at which the second bone contact portion projects, and the corner being on a side of the slider from which the second bone contact portion projects.

4. The measurement instrument for joint surgery according to claim 1, wherein the position display portion is provided with a gauge that is provided in one of the housing and the slider, and a reading position indicating portion that is provided in the other one of the housing and the slider and indicates a reading position in the gauge.

5. The measurement instrument for joint surgery according to claim 1, further comprising:

a drive mechanism that drives the slider so as to slide relative to the housing.

6. The measurement instrument for joint surgery according to claim 5, wherein the drive mechanism includes:

a driving force input portion to which a driving force in a rotational direction from outside is input; and a sliding drive portion that converts the driving force in the rotational direction, the driving force being input to the driving force input portion, into a driving force in a linear direction, and slides the slider relative to the housing.

* * * * *